United States Patent
Ross et al.

(10) Patent No.: US 8,065,035 B2
(45) Date of Patent: Nov. 22, 2011

(54) AUTOMATED MEDICATION HANDLING SYSTEM

(75) Inventors: Graham Ross, Poway, CA (US); Mark Corey Yturralde, San Diego, CA (US)

(73) Assignee: Carefusion 303, Inc., San Diego, CA (US)

(*) Notice: Subject to any disclaimer, the term of this patent is extended or adjusted under 35 U.S.C. 154(b) by 939 days.

(21) Appl. No.: 11/871,521

(22) Filed: Oct. 12, 2007

(65) Prior Publication Data
US 2008/0272138 A1 Nov. 6, 2008

Related U.S. Application Data

(60) Provisional application No. 60/915,623, filed on May 2, 2007.

(51) Int. Cl.
*G06F 17/00* (2006.01)
*G06F 7/00* (2006.01)
*B65B 61/02* (2006.01)
*B65G 1/00* (2006.01)

(52) U.S. Cl. ........ 700/224; 700/244; 700/241; 700/231; 700/236; 53/411; 414/273

(58) Field of Classification Search ................ None
See application file for complete search history.

(56) References Cited

U.S. PATENT DOCUMENTS

| | | | | |
|---|---|---|---|---|
| 5,468,110 A * | 11/1995 | McDonald et al. | ........... | 414/273 |
| 6,370,841 B1 * | 4/2002 | Chudy et al. | ................ | 53/411 |
| 7,040,504 B2 * | 5/2006 | Broadfield et al. | ............ | 221/98 |
| 7,111,780 B2 * | 9/2006 | Broussard et al. | ............ | 235/381 |
| 7,151,982 B2 * | 12/2006 | Liff et al. | ................ | 700/241 |
| 2005/0021173 A1 * | 1/2005 | Pinney et al. | ................ | 700/231 |
| 2006/0226167 A1 | 10/2006 | Broadfield et al. | | |
| 2007/0027577 A1 | 2/2007 | Lunak et al. | | |
| 2007/0185615 A1 * | 8/2007 | Bossi et al. | ................ | 700/244 |

FOREIGN PATENT DOCUMENTS

| | | |
|---|---|---|
| WO | WO 99/61324 | 12/1999 |
| WO | WO 2005/109119 | 11/2005 |

OTHER PUBLICATIONS

New Zealand Examination Report dated Apr. 6, 2011 citing US Patent 6370841 and US 5468110.

* cited by examiner

*Primary Examiner* — Gene Crawford
*Assistant Examiner* — Yolanda Cumbess
(74) *Attorney, Agent, or Firm* — McDermott Will & Emery LLP

(57) ABSTRACT

Described herein are embodiments of systems and methods for providing an automated medication handling system that can, among other things, single-dose package medications, store and dispense medications in a pharmacy, transport medications to a nursing unit or other remote location, store them at that remote location, and load them into a portable unit carried by a nurse, who may dispense the medication at a bedside.

24 Claims, 21 Drawing Sheets

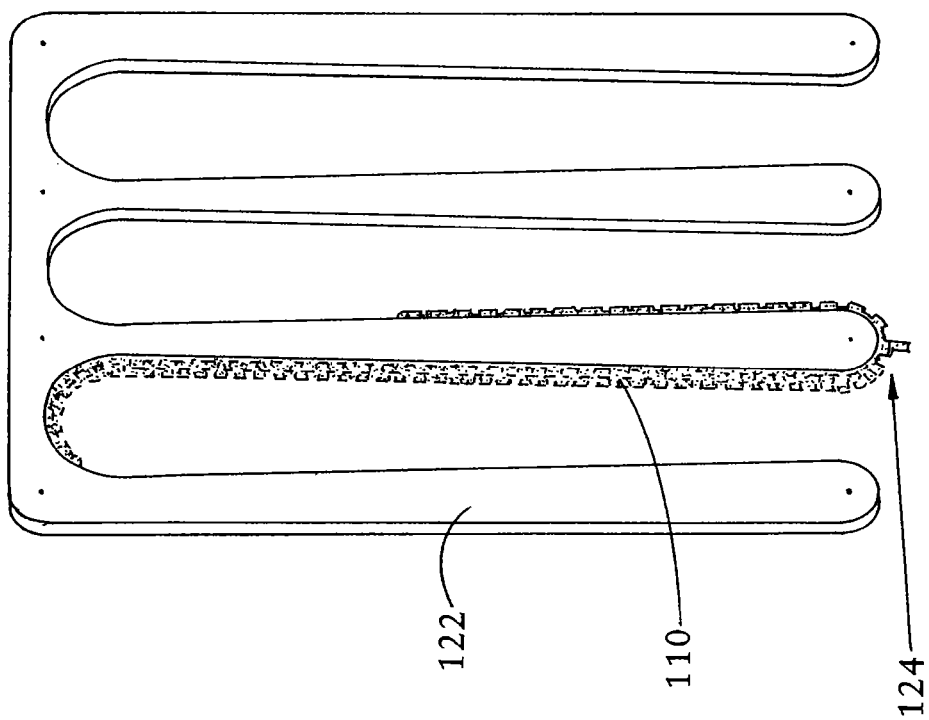

AUTOMATED MEDICATION HANDLING SYSTEM

CROSS-REFERENCES TO RELATED APPLICATIONS

This application claims priority benefit under 119(e) from U.S. Provisional Application No. 60/915,623, filed May 2, 2007, entitled, "TOTALLY AUTOMATED MEDICATION HANDLING SYSTEM," the entirety of which is hereby incorporated by reference.

STATEMENT AS TO RIGHTS TO INVENTIONS MADE UNDER FEDERALLY SPONSORED RESEARCH OR DEVELOPMENT

Not Applicable.

FIELD

The present disclosure relates generally to systems and methods for drug and health care supply distribution and replenishment, and more particularly to systems and methods for drug inventory management, drug information transfer, and drug packaging.

BACKGROUND

Health care providers, such as hospitals, utilize a pharmacist or pharmacy department within the hospital to coordinate the dispensing of drugs to patients of the health care institution. The pharmacists in such health care institutions are often burdened with the increasingly complex record keeping and inventory management that results from hospitals caring for hundreds, if not thousands, of patients every day.

The pharmacist's responsibility includes, among other things, filling individual patient prescriptions on a daily basis; maintaining sufficient inventory of each drug in order to have enough quantities of the drug in hospital stock to administer to patients on a daily basis; tracking of drug interactions to prevent a patient from being given a drug that has adverse affects when combined with other drugs; accounting for the purchase of drugs for use in the hospital; accounting associated with the giving of drugs to individual patients; distributing the drugs to the appropriate nursing stations within the hospital to suit each station's daily demands; tracking of drug expiration dates to rid inventories of expired drugs; and tracking of drug lot numbers, for example, in the event of a recall of a particular drug or drug lot number.

Health care providers, such as hospitals, often purchase drugs from drug distributors in bulk quantities (e.g., 100 single dose units of a particular drug). Health care supplies may be purchased in a similar fashion and the scope of the present disclosure is meant to include health care supplies, as well as drugs. While hospitals often purchase drugs in bulk due to manufacturer availability, drugs are nevertheless dispensed at the health care institution on a patient-by-patient basis in low dose quantities.

Some health care facilities include automated drug dispensing machines. These machines are often located at the point of use, such as at a caregiver's station in a patient unit. These machines are managed by caregivers in the pharmacy, who gather medications in the pharmacy, manually transport these medications to the machine, and manually load the machines. The machines have no specific knowledge of the medications and do not track lot numbers or expiration dates. Each medication dose must be manually inspected to determine if it has expired. In addition, any drugs that are removed from these machines and returned to the pharmacy must be manually inspected and loaded into the appropriate storage location in the pharmacy.

SUMMARY

Hospitals purchase and maintain large quantities of drugs until the drugs are eventually dispensed to the patients. Inventory turnover of drugs is usually measured in days, weeks or more. During such time, hospitals have to incur the associated expense of carrying this large inventory of drugs. Frequently, the result has been independent management of such large quantities, including unexplained loss of portions of the drugs in inventory, and even theft of portions of the inventory. In addition, the pharmacy department of the hospital has the extra burden of tracking the drugs dispensed for patient use, as well as tracking the drugs that the pharmacy is carrying in its inventory and monitoring expiration dates. These issues also apply to health care supplies in health care institutions.

The present disclosure is directed to systems and methods that overcome several of the above-mentioned problems associated with health care provider drug and supply distribution and maintenance. The present disclosure includes a unique form of drug packaging in combination with an automated medication handling system. This system consists of several subsystems that can be used independently or together to provide various services within a hospital. If all the subsystems are used, the result is total automation of drug handling within a hospital from the time that the drugs are single-dosed packaged in the pharmacy until the drug is delivered to a caregiver at the time of administration to a patient, and return of unused drugs to the pharmacy or disposal of expired drugs.

In some embodiments, the drugs received from the manufacturer are separated and packaged into machine-compatible single-dose containers. The containers are then provided with a label or tag that provides information relating to the drug within the container, and the information relating to the individual containers is stored in a processing unit. The single-dose containers are then placed in a storage dispenser and monitored by the processing unit. When a particular drug is needed, the location of the single-dose container is retrieved, and the system retrieves the container, at which point the container is placed in a retrieval unit (e.g., an automated dispensing machine) that can be accessed by the caregiver. The processing unit preferably retains information pertaining to the drug within each single-dose container or is configured to obtain information from the container that correlates to information contained in a database within or accessible to the processing unit. This information may include, among other things, the drug, the expiration date, drug dosage, location history, and even information relating to administration, such as recommended administration protocols or proscribed medicative combinations.

The processing unit preferably monitors the aging of the drugs within the single-dose containers and regulates usage of the drug. For example, monitoring can include whether a drug is used often in a first wing of a hospital but rarely used in a second wing of the hospital. In such a case, the processing unit may instruct that the drugs located in the first wing be periodically relocated to the second wing and be replaced with newer drugs, or drugs having a later expiration date. Additionally, the processing unit may further instruct that drugs having earlier expiration dates are placed such that they are used before drugs having later expiration dates. Accordingly, the system is able to regulate usage of the drugs such that wasted medications due to expiration and illicit usage are reduced, and the hospital is able to automatically or manually control location and administration of the single-dose containers.

In some embodiments, a system is provided for managing medications in a care facility. The system includes a packager at a first location that receives a plurality of medications and packages the medications into single-dose containers that are configured to be handled by a machine and a dispenser at a second location that provides the single-dose containers based on an expiration date of the medications.

Some embodiments include a transporter that conveys the single-dose containers from the first location to a storage unit or that conveys the single-dose containers from the first location to the second location. The single-dose containers can include an identifier that provides information about the medication within the container. In some embodiments, the identifier includes a barcode, a radio-frequency identification tag, or a two-dimensional matrix. The system can further include a patient-specific dispenser that receives the single-dose containers with medication corresponding to a patient's prescriptions. In some embodiments, the dispenser is capable of collecting and dispensing the expired medications within the system.

In some embodiments, a single-dose container is provided for protecting and transferring medications therein by a machine. The container preferably includes first and second substantially rigid portions that are configured to couple together and form a machine-compatible container having a hollow enclosure that is sized to enclose a single dose of medication, an identifier that is provided with at least one of the first and second substantially rigid portions that provides access to information relating to medication within the hollow enclosure, and an indicator that provides information relating to decoupling of the first and second substantially rigid portions.

In some embodiments, the identifier includes at least one of a barcode, a radio-frequency identification tag, and a two-dimensional matrix. Some embodiments provide that at least one of the substantially rigid portions comprises a biodegradable material. The indicator can prevent, in some embodiments, recoupling of the first and second substantially rigid portions following decoupling of the two portions. In yet further embodiments, the first and second substantially rigid portions include colors that correspond to characteristics of the medication contained therein.

Also disclosed herein are methods of managing medications in a care facility. In some embodiments, the method includes packaging medication into a single-dose container that is configured to be compatible with handling by a machine, providing an identifier with the single-dose container that provides information relating to the medication within the container, transporting the single-dose container by machine to a storage facility, and relocating the single-dose container by machine based on the information provided by the identifier.

Some methods provide that the information provided by the identifier is an expiration date of the medication. Some methods provide that the information is at least one of a drug name, a dosage, a manufacturer, and a lot number. Relocating the single-dose container can be, in some methods, in response to a recall of the medication. Further methods include dispensing the single-dose container for administration to a patient, which may include removing the medication from the single-dose container.

For purposes of summarizing the disclosure, certain aspects, advantages, and novel features of the disclosure have been described herein. It is to be understood that not necessarily all such advantages may be achieved in accordance with any particular embodiment of the disclosure. Thus, the disclosure may be embodied or carried out in a manner that achieves or optimizes one advantage or group of advantages as taught herein without necessarily achieving other advantages as may be taught or suggested herein.

BRIEF DESCRIPTION OF THE DRAWINGS

A general architecture that implements various features of the disclosure will now be described with reference to the drawings. The drawings and the associated descriptions are provided to illustrate embodiments of the disclosure and not to limit the scope of the disclosure. Throughout the drawings, reference numbers are re-used to indicate correspondence between referenced elements.

FIG. 16 depicts embodiments of a rack of tracks depicted in FIG. 15.

DETAILED DESCRIPTION

Figure 1:
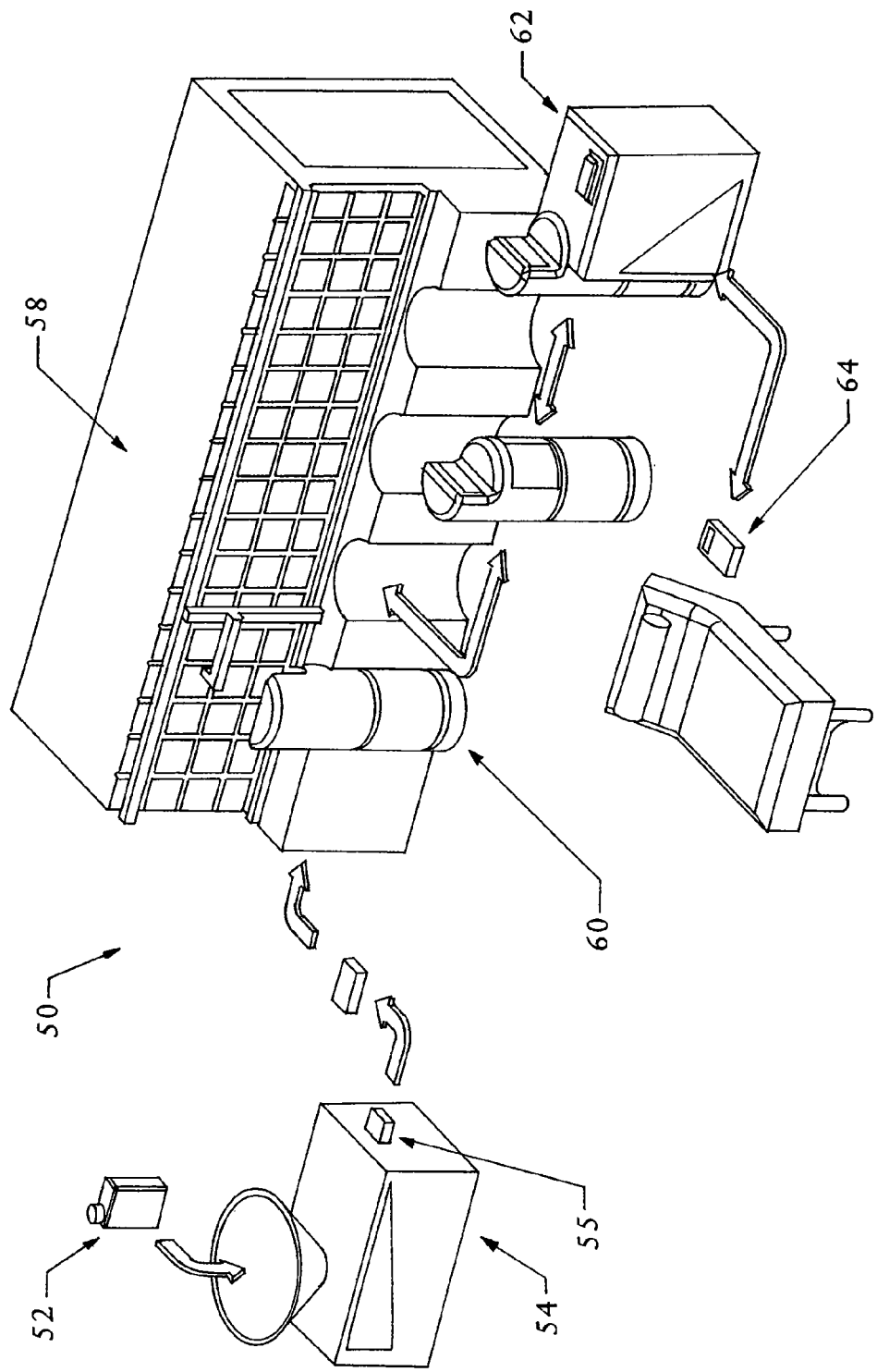
FIG. 1 illustrates a schematic depiction of one embodiment of a system for distributing and monitoring drugs described herein.

Described herein are embodiments of a system of automated products that can single-dose package medications, store and dispense them in a pharmacy, transport them to a nursing unit or other remote location, store them at that remote location, and load them into a portable unit carried by a nurse, which may dispense the medication at a bedside. Each subsystem can interact with other subsystems to transfer medications and information. Each medication is preferably contained in a machine-compatible container that includes machine readable information with the container or medication. Some of these system components can read the information from the medication and automatically manage the medication. Accordingly, manual handling of the medication is reduced or eliminated between the time the bulk container is emptied into the single-dose packager and dispensing the single-dose into the nurse's hand at the bedside.

In some embodiments, one or more of the subsystems can be used as stand-alone units to automate a subset of the total medication handling process in a hospital. Multiple subsystems could be installed with only select functions performed manually. For instance, the transport of medications from a central storage unit in the pharmacy to a remote storage unit may be done manually, eliminating the need for automated delivery systems between the pharmacy and the remote storage unit.

The systems described herein provide the ability to package medications by an individual-dose packager in single-dose containers including data storage information. Following the single-dose packaging, the system provides a transfer subsystem to move the individual doses from the packager to a dispenser. The system further provides a storage cabinet with individual medication dispensers that incorporate the ability to accept bulk, mixed medications and sort them into individual dispensers. The system is also able to dispense arbitrary selections of medications into a single container for delivery to a remote dispensing location. Some embodiments provide a transport robot that can accept containers, or individual medications, from the storage cabinet and transport them to a second storage device at a remote dispensing location. The transport robot is further able to accept containers, or individual medications, that are to be returned to the pharmacy or are to be relocated to another remote dispensing location or storage device.

In some embodiments, the remote location storage device can be a MEDSTATION® provided by Cardinal Health. The remote location storage device is preferably configured to accept a mixed bin of medications and to store the medications in a random-access fashion. The storage device can also select and fill the bin with medications that are to be returned to the pharmacy or are to be relocated to another dispensing location or storage device.

Further embodiments provide a portable device that is carried by the nurse and which docks with the remote location storage device. In some embodiments, the storage device loads and unloads the portable unit so that the unit contains only the medications currently ordered for dispensing to the nurse's patients within, for example, a specified time (e.g., during the nurse's shift).

Among other advantages, the systems and methods described herein facilitate management of medications at a health care facility. For example, managing medications in a hospital is a very labor-intensive process, and many of the activities relating to management of the medications must be performed by licensed pharmacists. With a shortage of pharmacists, the workload of the pharmacy staff is ever-increasing. The systems and methods described herein provide the potential to improve patient safety and to offload some activities from the pharmacists and allow them to focus their time on activities that more effectively utilize their skills.

As used here in, the terms "medication" and "drug" are intended to have their ordinary meaning, which includes, without limitation, any therapeutic agent, or substance containing a therapeutic agent.

With initial reference to FIG. 1, a medication handling system 50 in accordance with embodiments disclosed herein is schematically illustrated. For example, FIG. 1 depicts methods and apparatus for regulating and monitoring the distribution of drugs in a care facility. The pharmacy often receives medication doses, such as pills, in a bulk drug container 52. The medication doses within the bulk drug container 52 are preferably deposited into a drug packager 54. The drug packager 54 packages the medication doses into single-dose containers 56 (FIG. 2) and preferably provides a label 57 or other information-containing tag with the single-dose container 56 that provides information relating to the medication inside the single-dose container 56. The single-dose containers 56 are then transported to a single-dose dispenser 58. The single-dose containers 56 can be conveyed via a transport robot 60 that receives the single-dose containers 56 from the drug packager 54 and transports them in a transfer container 55 to the single-dose dispenser 58.

The single-dose dispenser 58 holds the single-dose containers 56 until it is determined that the single-dose containers 56 are to be dispensed in preparation for administration to a patient. Upon such determination, the single-dose containers 56 are conveyed to a remote dispensing location and stored within a storage device 62. In some embodiments, the transport robot 60 conveys the single-dose containers 56 from the single-dose dispenser 58 to the storage device 62. The storage device 62 is preferably in the vicinity of a nursing station, providing ready access to nurses or other caregivers operating near the storage device 62. The single-dose containers 56 from the single-dose dispenser 58 are transferred by the transport robot 60 to the storage device 62. At this time, the storage device 62 can also transfer less-frequently used or older medications to the transport robot 60 for returning to the single-dose dispenser 58 or relocation elsewhere within the care facility.

The storage device 62 can provide the single-dose containers 56 directly to the nurses operating in the vicinity of the storage device 62, or the storage device 62 can be configured to provide the single-dose containers 56 to a dockable hand-carried dispenser 64. In some embodiments, the hand-carried dispenser 64 can be programmed to receive medications that will be or likely will be used by patients a particular nurse is caring for during a given time. The nurse holds the hand-carried dispenser 64 as she makes her rounds to several patients, and the hand-carried dispenser 64 provides access to the single-dose containers 56 corresponding to the medications that are to be administered to that nurse's patients.

In some embodiments, the hand-carried dispenser 64 includes mechanisms for verifying that the correct drugs are being dispensed from the storage device 62 and for removing the drugs from their single-dose containers 56 in preparation for administration to the patient. In yet further embodiments, the hand-carried dispenser 64 is configured to identify the medications being provided to an individual patient and reduce the likelihood of providing incompatible medications to a patient. For example, the hand-carried dispenser 64 can be programmed to identify combinations of medications that may have adverse side effects and alert the nurse or other caregiver of the potential incompatibility of the medications. The alert may be a visual light or message on the hand-carried dispenser 64 or an audible alarm sounded by the hand-carried dispenser 64.

In some embodiments, a system is provided without one or more of the above mentioned subsystems. For example, in some embodiments, the transport robot 60 is configured to convey the single-dose containers 56 from the drug packager 54 directly to the storage device 62, completely bypassing the single-dose dispenser 58. In yet other embodiments, the transport robot 60 is configured to convey the single-dose containers 56 from the drug packager 54 directly to the hand-carried dispenser 64, thus bypassing both the single-dose dispenser 58 and the storage device 62. In some embodiments, the transport robot 60 is configured to convey the single-dose containers 56 from the single-dose dispenser 58 to the hand-carried dispenser 64, thus bypassing the storage device 62.

The medication handling system 50 preferably includes a processor 51 (FIG. 23) that retains the information of each single-dose container 56 that enters the system 50. The processing unit 51 preferably monitors, among other things, the expiration date of the medications within the system 50. As the expiration date of medications approaches, the processing unit is configured to instruct the medication handling system 50 to position the older medications and locations within the care facility where the medications are likely to be used. The processing unit can further instruct the system 50 to place the older medications into the hand-carried dispensers 64 to increase the likelihood of using the medication prior to the expiration date. In some embodiments, the processing unit can instruct the system 50 to retrieve all medications that have expired or that are recalled for disposal. Accordingly, the system can perform the otherwise laborious process of removing expired medication from the health care facility's inventory, saving the time and expense otherwise required to be performed by a licensed pharmacist. As well, the system 50 reduces the amount of wasted medications by managing the medications so that the medications closest to expiring are dispensed before those medications with greater time to expiration. The individual components of the system 50 will now be discussed.

The single-dose container 56 allows automated drug handling to be achieved. In some embodiments, the container 56 is made of a rigid material with internal features that enclose the medication, restrict movement of the medication, or that otherwise reduce the likelihood of the medication from being damaged during handling by a machine. The single-dose containers 56 are preferably configured to provide visual indication of tampering or opening, such as a seal. In some embodiments, the single-dose containers 56 are returned, after having been opened, back to the drug packager 54, which may be configured to reuse the single-dose containers 56 in subsequent applications. In other embodiments, the single-dose containers 56 are configured to not be reusable, and are destroyed or disposed of following a single use.

Figure 2:
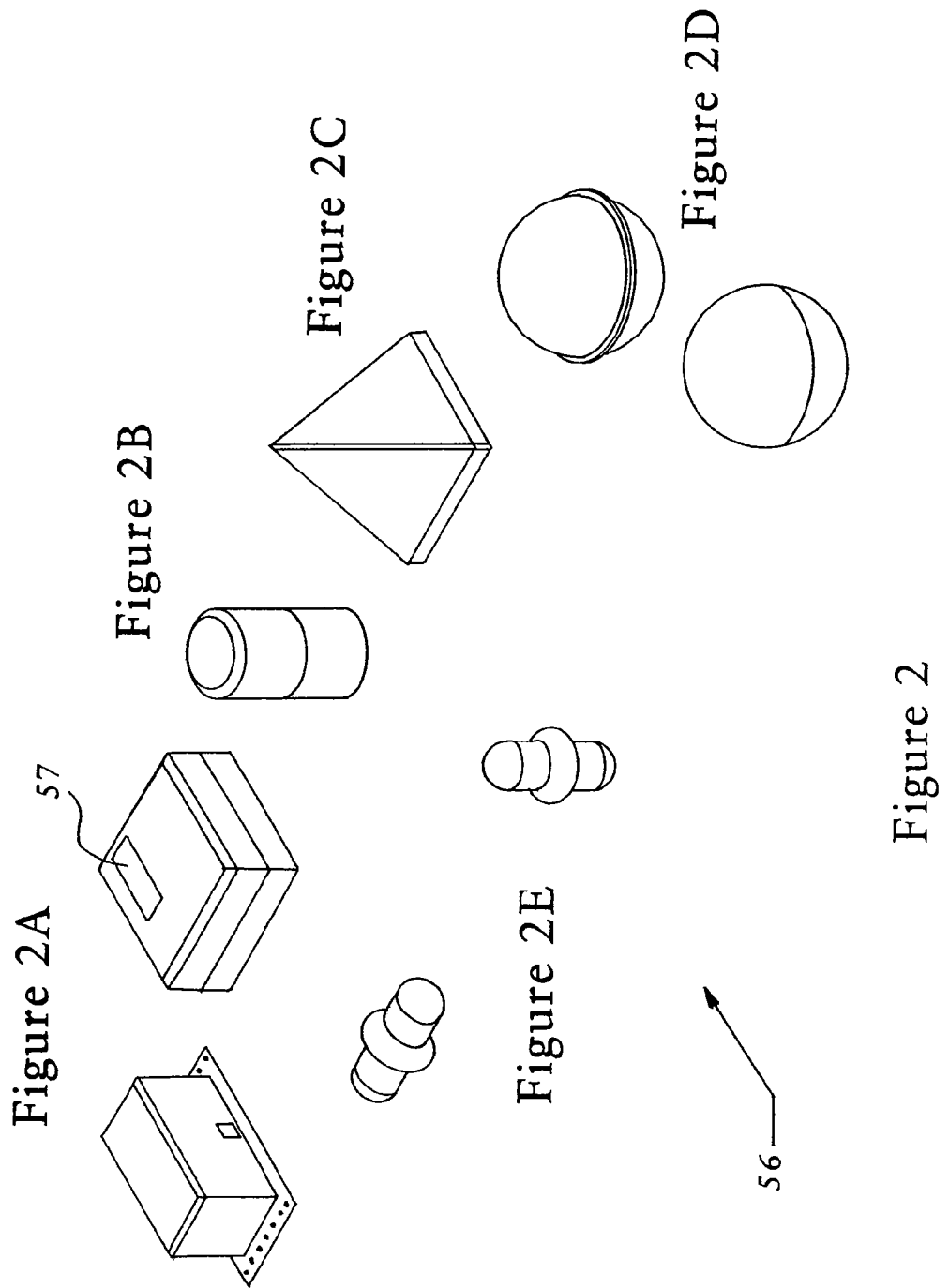
FIG. 2A depicts orthogonally-shaped embodiments of drug containers that can be used in connection with the drug distribution and monitoring systems and methods described herein.
FIG. 2B depicts embodiments of a cylindrical drug container that can be used in connection with the drug distribution and monitoring systems and methods described herein.
FIG. 2C depicts embodiments of a pyramidal drug container that can be used in connection with the drug distribution and monitoring systems and methods described herein.
FIG. 2D depicts embodiments of spherical drug containers that can be used in connection with the drug distribution and monitoring systems and methods described herein.
FIG. 2E depicts further embodiments drug containers that can be used in connection with the drug distribution and monitoring systems and methods described herein.

FIG. 2 illustrates a plurality of different shapes and sizes that can be used as containers for the medications. As illustrated in FIGS. 2A-2E, the container 56 can be orthogonally-shaped (FIG. 2A), cylindrical (FIG. 2B), pyramidal (FIG. 2C), spherical (FIG. 2D), or other regular or irregular shapes (e.g., FIG. 2E) and sizes. In some embodiments, a common shape is used for all containers 56, such as a spherical shape, and a size is selected that will accommodate substantially all the drugs that are used in the system. In some embodiments, the system 50 may accommodate multiple-sized single-dose containers 56. For example, in some embodiments, small containers may contain single pills while large containers may contain tubes of ointment or bottles of liquid. Each of these shapes are configured for machine-handling.

In some embodiments, the containers 56 are made of a material, such as a durable plastic, that can be handled by machines while protecting the drug within the container 56. The material should be substantially impermeable to moisture to provide adequate storage life for the drug. In some embodiments, the container 56 is made of a biodegradable material, such as corn starch, that will minimize the environmental impact of large numbers of the disposable containers 56.

The single-dose containers 56 are preferably configured to include an identifier that can be read or accessed and which provides information relating to the medication contained within the container 56. For example, the identifier can be a label 57 having a printed barcode or 2D data matrix that contains a code that is readable by a camera and accessible through the processing unit. In some embodiments, the identifier can provide a 3D code that is readable by one or more cameras, such as dimples that are imprinted on the container 56. In other examples, the identifier can be an electronic memory device, such as an RFID tag, that stores information relating to the medication on the container 56 itself. In some embodiments, the electronic memory device can communicate through direct contact, with one or more electrical contacts, or through wireless communication. The information relating to the medication can include, among other things, a drug name, dosage, manufacturer, lot number, and expiration date. The information could be programmed and updated at appropriate times during handling, possibly even having a particular dose of medication assigned to a specific patient before the drug leaves the pharmacy.

The single-dose containers 56 may also be color coded to indicate basic characteristics of the drug inside. For example, a red container may indicate a controlled narcotic while a blue container could indicate a painkiller. Therefore, a container that is half red and half blue might be a narcotic painkiller, while a container that is half white and half blue might indicate a non-narcotic painkiller, such as ibuprofen.

The drug packager 54 accepts bulk quantities of the components of the single-dose containers 56 as well as a quantity of medications to be packaged. In some embodiments, the packager 54 includes input devices to read the drug information off the bulk container 52 or to have the data input directly by an operator. The packager 54 also preferably includes tools to encode the appropriate data from the bulk container 52 onto the single-dose containers 56. This may be a printer for a barcode or a 2D matrix or an RFID transponder to program RFID tags embedded in the single-dose containers 56. The packager 54 preferably directs the filled single-dose containers 56 to an output location of the packager 54.

In some embodiments, the packaging of the medications, or other components that are placed in the single-dose containers 56, occurs at a manufacturing facility apart from the care facility. For example, in some embodiments, the medication doses are sold to the care facilities already within the single-dose containers 56. In these embodiments, the packager 54 operates to place the medication doses it receives in bulk into the individual single-dose containers 56 and seals the single-dose containers 56 in a manner that would reveal tampering or opening. The packager 54 also labels the single-dose containers 56 as discussed above.

Following the packaging of the medication doses within the single-dose containers 56, the single-dose containers 56 are prepared for dispensing in a pharmacy or care facility. In some embodiments, the single-dose containers 56 include a label 57 therewith to provide indication of the contents of the single-dose container 56. Through the label 57, a processor 51 (depicted in FIG. 23) identifies and records the contents of each single-dose container 56 and the location of each container 56 within the system 50. Once the medication doses are packaged and identified, the single-dose containers 56 can be transferred to the single-dose dispenser 58. In some embodiments, the containers 56 are transferred from the packager 54 to the single-dose dispenser 58 in a transfer container 55. In some embodiments, a transporter, or transport robot 60, can convey the transfer containers 55 to the single-dose dispenser 58. In other embodiments, the single-dose containers are placed directly into the single-dose dispenser 58 from the pharmacy or retailer.

The single-dose dispenser 58 operates as a general storage subsystem by receiving the single-dose containers 56 and holding them until they are dispensed to various locations within the care facility. The single-dose dispenser 58 includes, in some embodiments, a detector that reads the information contained by the label 57 of the container 56 and provides that information to the processor 51 (depicted in FIG. 23). For example, while the single-dose dispenser 58 holds the single-dose containers 56, the dispenser 58 can conduct a select or general analysis of all the containers 56 within the dispenser 58. This analysis can be performed when, for example, it is desired to ensure that a database containing information regarding the containers 56 is accurate. Moreover, identification of each container 56 can be performed after the containers 56 are located in the dispenser 58. For example, a random supply of medication doses can be provided to the single-dose dispenser 58, and the dispenser 58 can obtain information regarding each of the containers 56 during or after the doses are provided to the dispenser 58.

Embodiments of components of the single-dose dispenser 58 are described below. For example, described below are trays that are configured to retain or hold the containers 56, systems for manipulating the containers 56, systems for obtaining information regarding the containers 56, and embodiments relating to preparing the containers 56 for dispensing from the dispenser 58.

Figure 3:
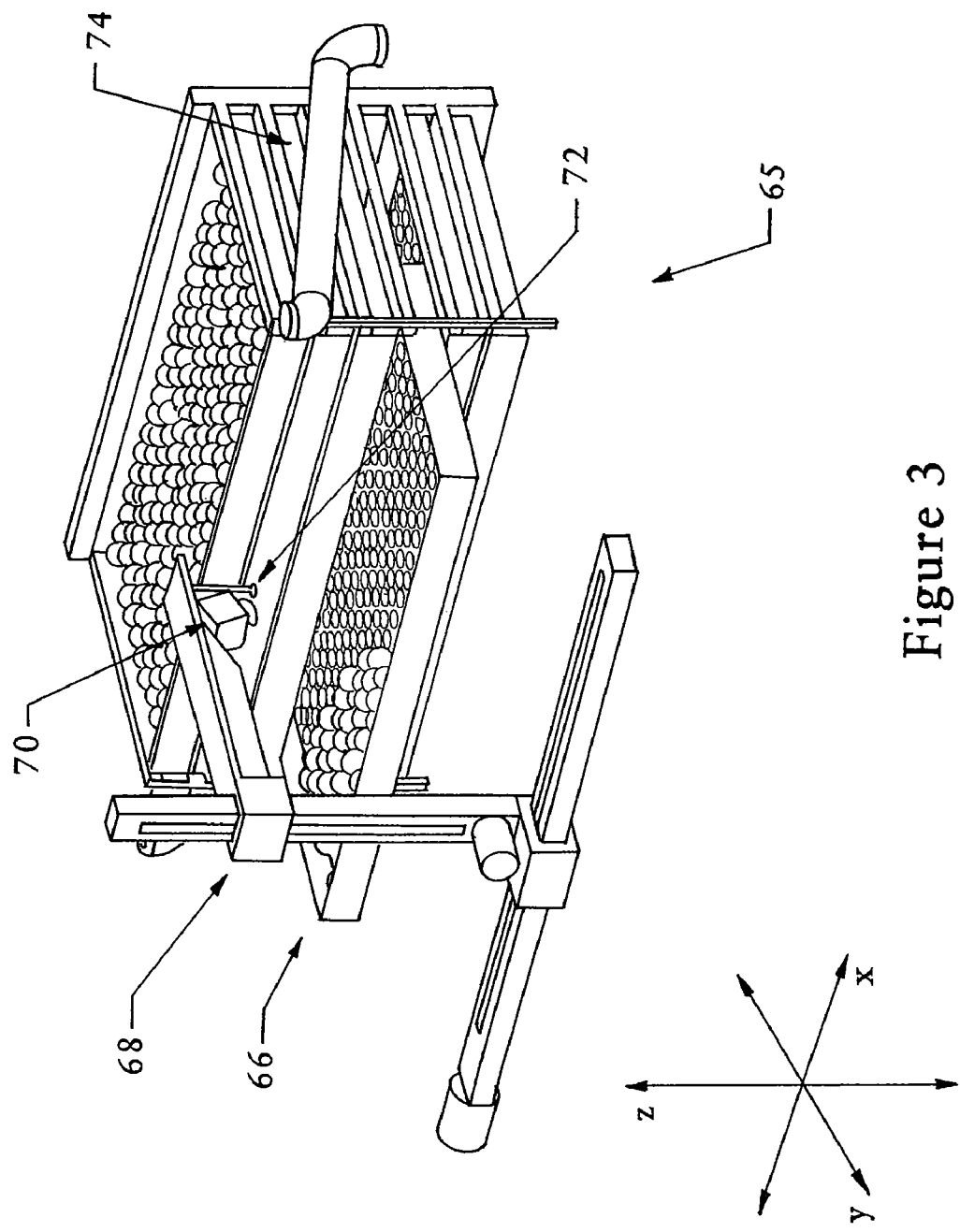
FIG. 3 illustrates embodiments of spherical container moving trays and an actuating arm that manipulates the spherical containers.

With reference to FIG. 3, embodiments of a module 65 containing modular trays 66, employed within the dispenser 58, are illustrated. The modular trays 66 depicted in FIG. 3 are configured to handle spherical single-dose containers 56, although modifications in the trays 66 can be made to provide handling of other single-dose containers 56, some of which are depicted above in FIGS. 2A-2E. As an example, the trays 66 depicted in FIG. 3 are movable in a y-direction with respect to an arm 68 that is movable in both the x- and z-directions. The arm 68 preferably includes a camera 70 and a picker 72 that are used in connection with the single-dose containers 56. The camera 70 is preferably configured to read the label 57, or other identifier, located on the single-dose container 56 to confirm selection of the proper container 56 or to otherwise obtain information regarding the container 56. Another device for scanning and identifying labels 57 or other identifiers may be used, such as a bar code scanner or RFID reader. The picker 72 is preferably configured to couple with the container 56, for example, by adhesion or vacuum, and to move the container 56 to a guide tube 74 that leads to a transport box (not shown in FIG. 3), which can be another modular tray 66, that is accessed by a transporter, which, in some embodiments, is the transport robot 60. The module 65, preferably comprises a plurality of modular trays 66 and can be oriented in vertical stacked relationship, as illustrated in FIG. 3. Multiple modules 65 can be operated in parallel to increase overall speed in filling a transport box or a second modular tray, not shown in FIG. 3.

In operation, the processor 51 (depicted in FIG. 23) determines which module 65, which tray 66, and a location a desired single-dose containers 56 resides on. The arm 68 and tray 66 are moved to the requested location, and the camera 70 verifies the label 57 on the selected location to be the correct single-dose container 56 having the desired medication. The arm 68 moves the picker 72 to grip the single-dose container 56. The arm 68 then raises the container 56 up and moves to drop the container into the guide tube 74. Once in the guide tube 74, the container 56 travels down to the transport box, or modular tray (not illustrated in FIG. 3).

In some embodiments, a modular tray 66 is provided to the dispenser 58. The modular tray 66 can contain a variety (e.g., a random selection) of medication doses within containers 56. Upon receipt by the dispenser 58, the modular tray 66 is positioned in a module 65, and information from labels 57 or other identifiers of the containers 56 is obtained by the camera 70 or other information-obtaining device. When a request for a specific medication dose stored on the modular tray 66 is provided to the dispenser 58, the modular tray 66 and the container 56, or containers, containing the medication dose is identified and located. The arm 68 positions the picker 72 to grasp the container 56, and then positions the picker 72 with the container 56 to deposit the container 56 within the drop tube 74. The drop tube 74 preferably leads the container 56 to a dispensing modular tray 76 (FIG. 7B) that is configured to be dispensed or transported to a location within the care facility. When the dispensing modular tray 76 has obtained the containers 56 containing the requested medication doses from the drop tube 74, the dispensing modular tray 76 is conveyed, via a transporter or transport robot 60, to the requested location, whereat the containers 56 are prepared for dispensing to caregivers.

Figure 4:
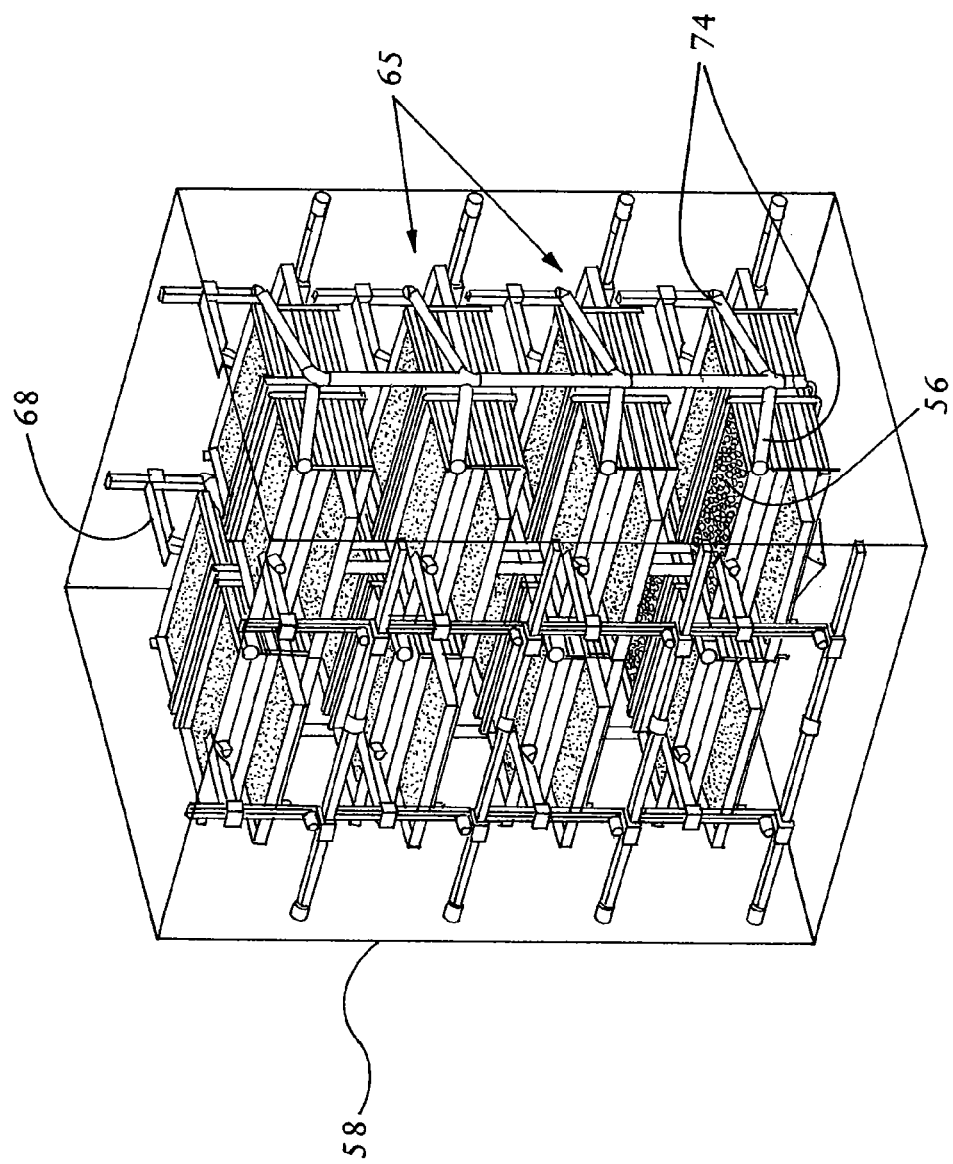
FIG. 4 illustrates embodiments of a system section for a spherical dose container that includes multiple embodiments of moving trays and actuating arms depicted in FIG. 3.

FIG. 4 depicts a plurality of modules 65 that are coupled together for handling single-dose containers 56 within the single-dose dispenser 58. In the illustrated embodiment, modules 65 are stacked vertically and horizontally, each module 65 having its own arm 68 for identifying and retrieving the single-dose containers 56. In other embodiments, a single arm 68 services multiple modules 65. Guide tubes 74 from multiple modules 65 can be conjoined to provide single-dose containers to the dispensing modular trays 76 (FIG. 7B).

Figure 5:
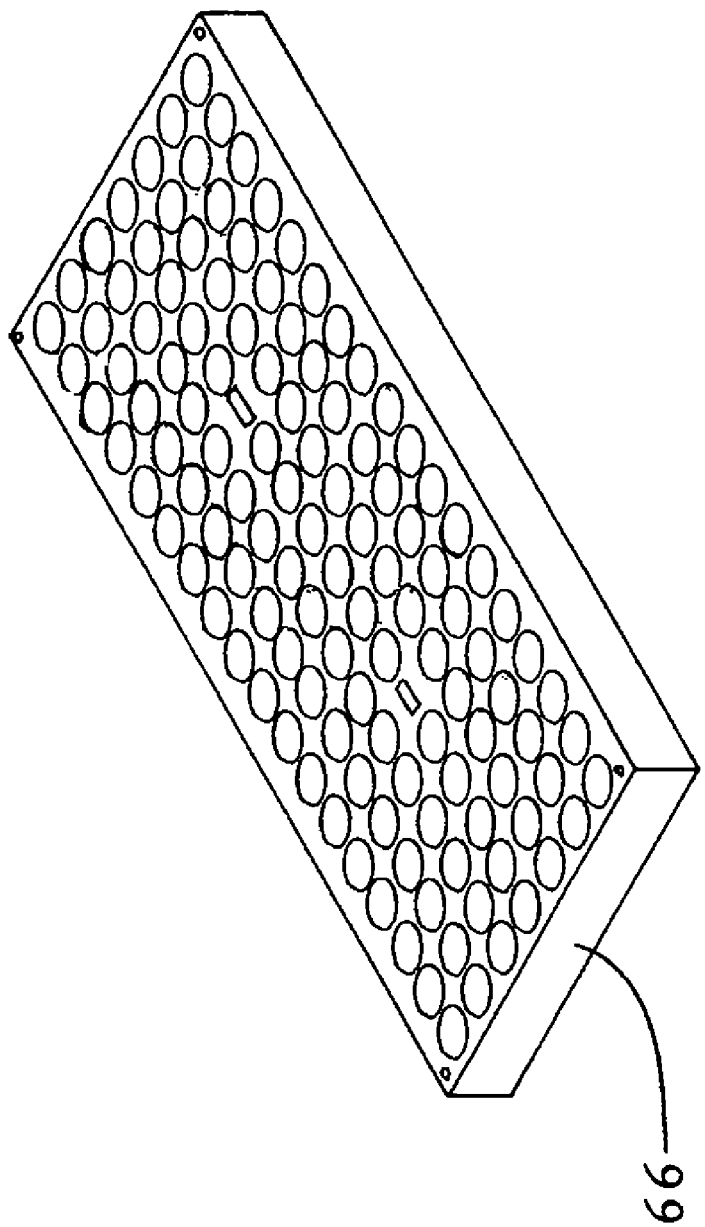
FIG. 5 depicts a tray for cylindrical containers.
Figure 6:
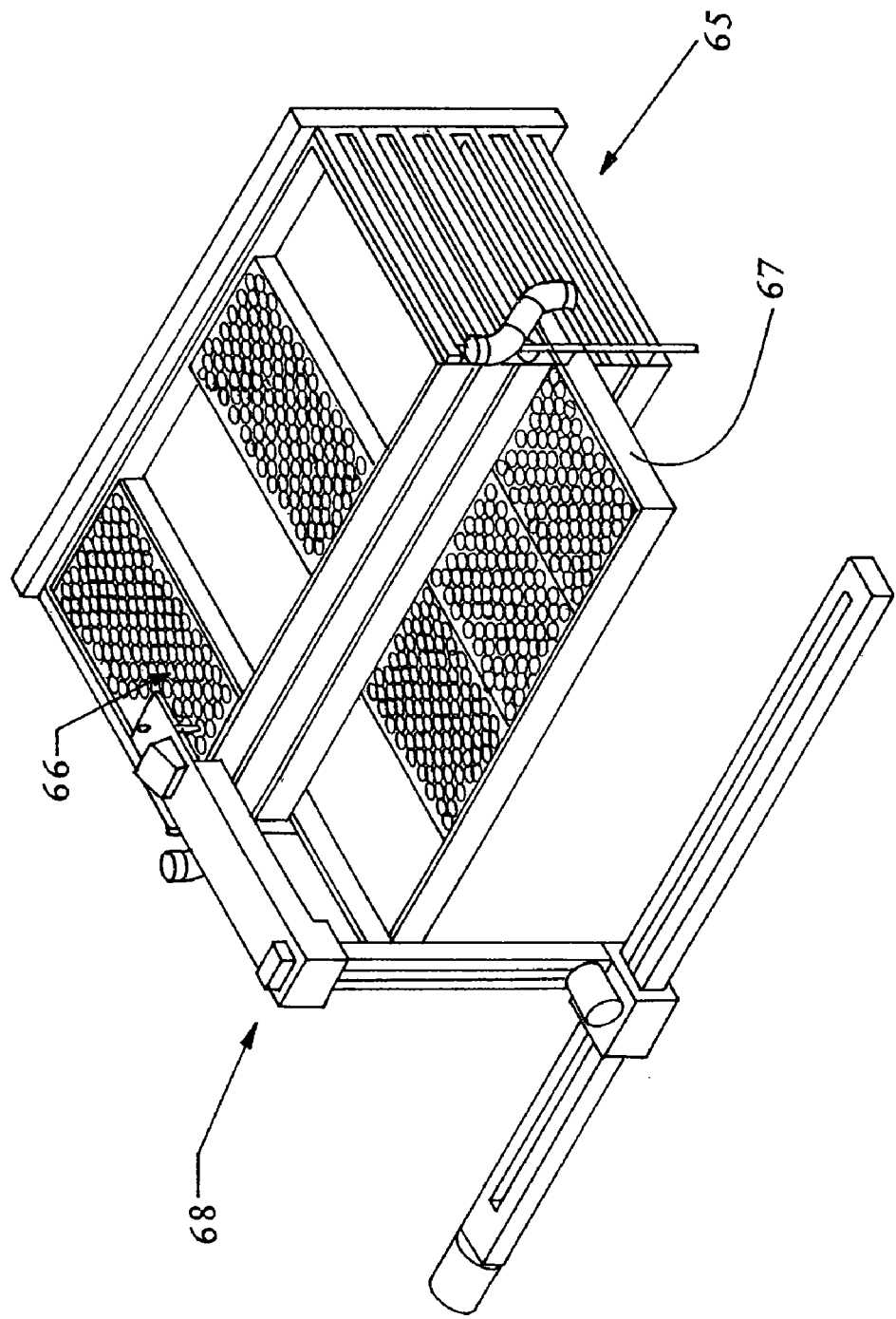
FIG. 6 illustrates a plurality of modular trays for cylindrical single-dose containers.

FIG. 5 illustrates another embodiment, in which the modular tray 66 is configured for handling cylindrical containers 56. Similar to the trays 66 discussed above for handling spherical single-dose containers 56, the cylindrical trays 66 are configured to operate in connection with an arm 68 having a camera 70 and a picker 72, as illustrated in FIG. 6. FIG. 6 depicts embodiments of a plurality of the modular trays 66 positioned within a module 65. The plurality of modular trays 66 are positioned on movable trays 67 that slide out of the module 65 when a modular tray 66 on the movable tray 67 is accessed. When access to the modular tray 66 is no longer desired, the movable tray 67 slides back into the module 65 to store the plurality of trays 66 therein.

Dispensing the single-dose containers 56 into the guide tube 74 will conduct the single-dose containers 56 to be positioned into dispensing modular trays 76 at the dispenser. The dispensing modular trays 76 are then preferably routed and transferred to an appropriate transport robot 60 for distribution of the dispensing modular trays 76 to locations within the care facility. Dispensing the single-dose containers 56 is thus preferably performed in each module 65 by moving trays 66, gripping the selected single-dose containers 56, and dropping the single-dose containers 56 into the drop tube 74.

Figure 7:
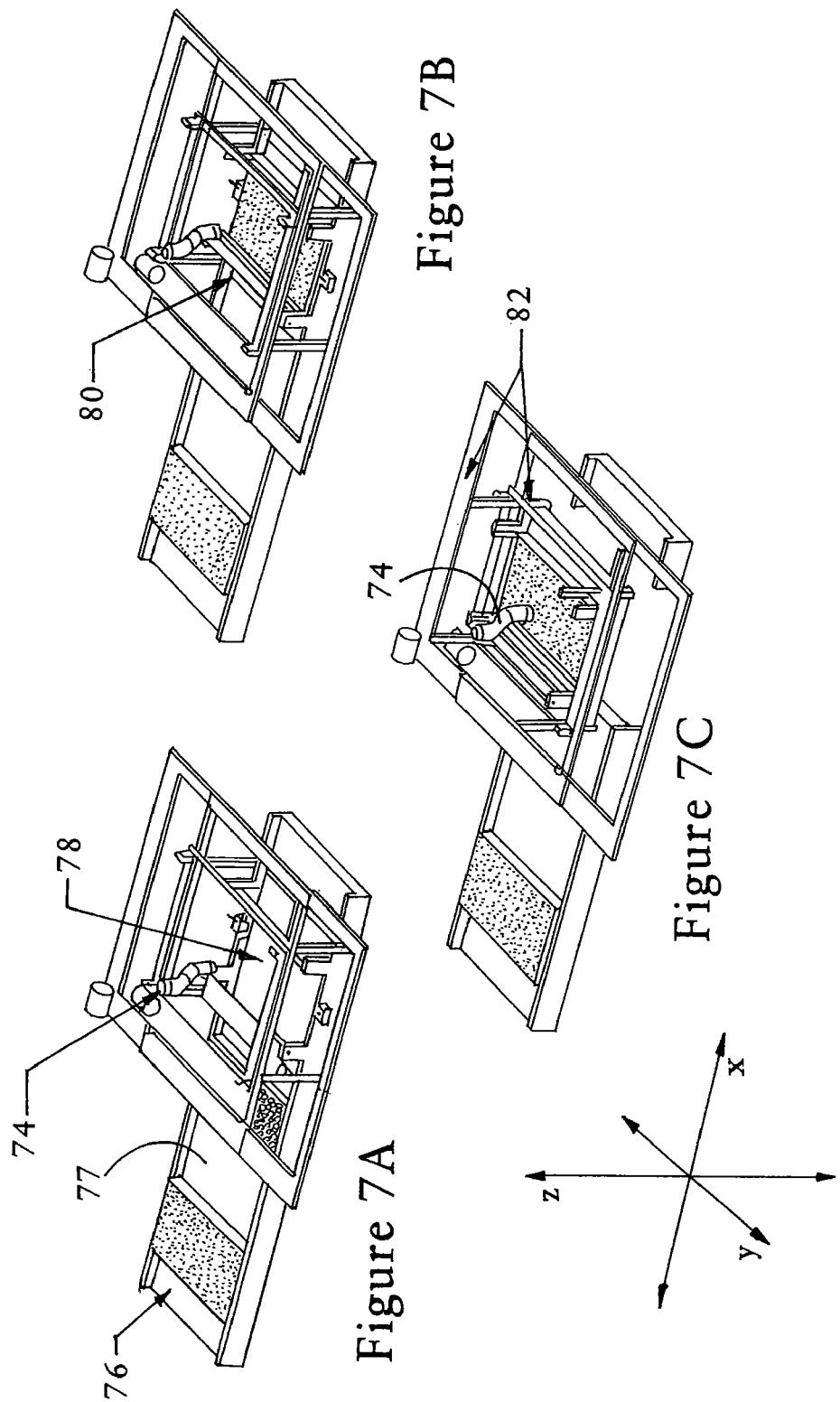
FIGS. 7A-C illustrate embodiments in which single-dose containers are dispensed into a modular tray.

FIGS. 7A-7C depict embodiments and steps of the process by which the single-dose containers 56 are routed from the drop tube 74 into a position on a dispensing modular tray 76 for further handling. Unlike the modular trays 66 that remain within the dispenser 66, the dispensing modular trays 76 are transported through the health care facility. In some embodiments, however, the same tray can operate as both a modular tray 66 and a dispensing modular tray 76. An empty dispensing modular tray 76 is brought by a conveyer track 77 into an initial dispensing position onto an elevator track section 78, as shown in FIG. 7A. An alignment gate 80 closes to properly position and orient the dispensing modular tray 76, as illustrated in FIG. 7B. The elevator track section 78 moves upward until the modular tray 76 is located just below the drop tube 74, as illustrated in FIG. 7C. In this position, an XY table 82 is unlocked, and the XY table 82 positions the dispensing modular tray 76 such that as single-dose containers 56 exit the drop tube 74, they are deposited into specified empty positions on the dispensing modular tray 76. In some embodiments, the XY table 82 is stepped so that the dispensing modular tray 76 may be filled. When the dispensing is complete, the XY table 82 is moved back into the locked position and the elevator section 78 is lowered to bring the dispensing modular tray 76 back to the conveyer track 77, as depicted in FIG. 7B. The alignment gate 80 is opened to release the dispensing modular tray 76, and the dispensing modular tray 76 is then moved by the conveyer track 77 toward a position that the dispensing modular tray 76 can be accessed by a transporter, such as the transport robot 60 depicted in FIG. 1.

Figure 8:
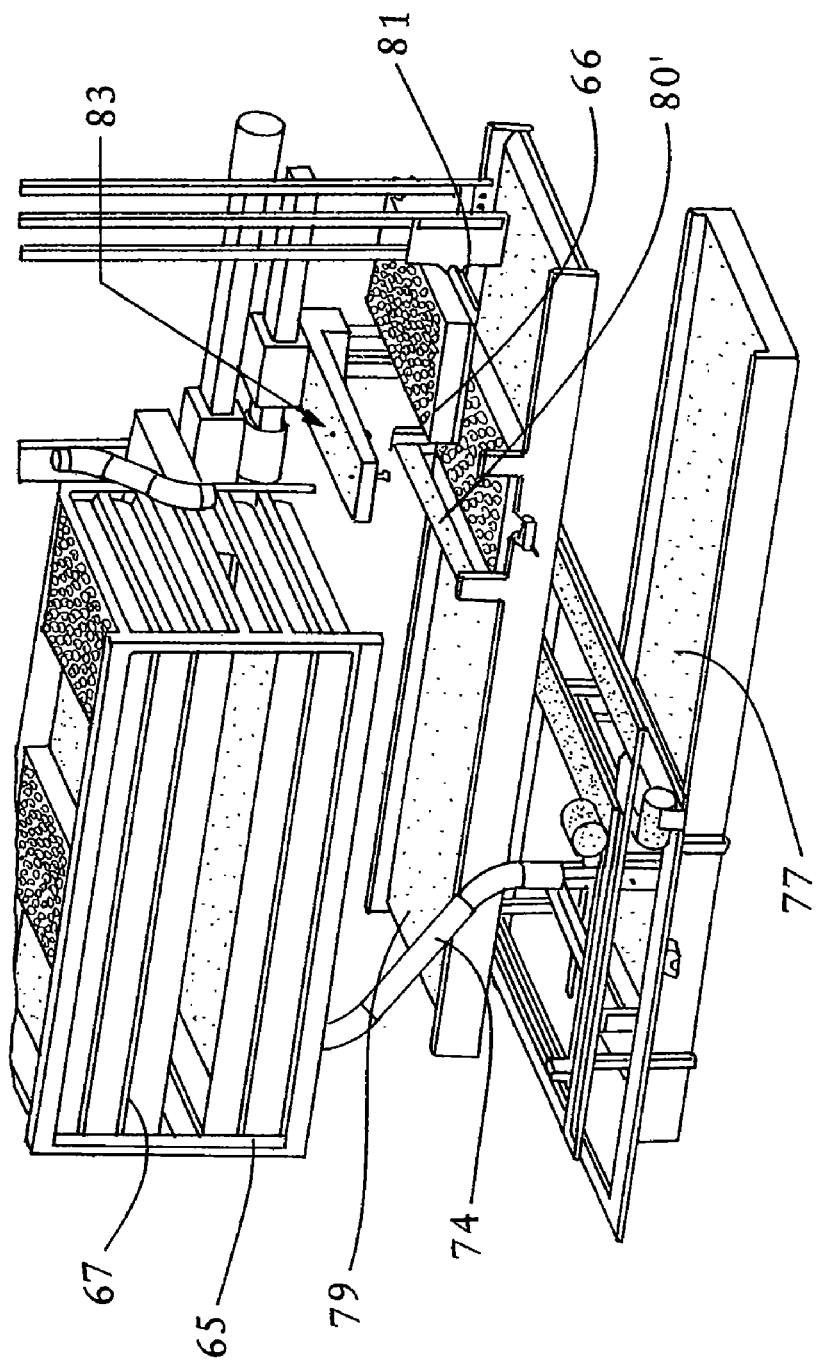
FIG. 8 illustrates a loading elevator and dispensing station.

FIG. 8 illustrates embodiments and steps of the combined loading process, by which modular trays 66 are positioned in modules 65, and dispensing process, by which single-dose containers 56 are retrieved and provided to the dispensing modular trays 76. In the illustrated embodiment, both the loading and dispensing processes occur within the single-dose dispenser 58. During the loading process, single-dose containers 56 are provided in a modular tray 66 upon a loader track 79. The modular tray 66 is conveyed along the loader track 79 to a loader alignment gate 80'. The loader alignment gate 80' aligns, orients, and secures the modular tray 66 with respect to a loader arm 83, whereupon the loader arm 83 engages the modular tray 66 and transfers the modular tray 66 to and from a loader elevator platform 81. The loader elevator platform 81 positions the modular tray 66 within the module 65 (e.g., on a movable tray 67) for storing the single-dose containers 56 until the single-dose dispenser 58 is requested to retrieve the single-dose containers 56.

During the dispensing process, as explained above, for example, with respect to FIGS. 3 and 6, the single-dose containers 56 are retrieved from the modular trays 66 and deposited into drop tubes 74. For example, the single-dose containers 56 are dispensed by the arm 68 that accesses an open tray 66 and using its camera 70 to verify the container 56, and then employing the picker 72 to grip the single-dose container 56, as explained above with respect to FIGS. 3 and 6. The single-dose container 56 is then placed into the drop tube 74, where it is conveyed to a dispensing modular tray 76 provided by the conveyer track 77. The dispensing modular tray 76 is preferably positioned and filled as described above with respect to FIGS. 7A-7C.

Figure 9:
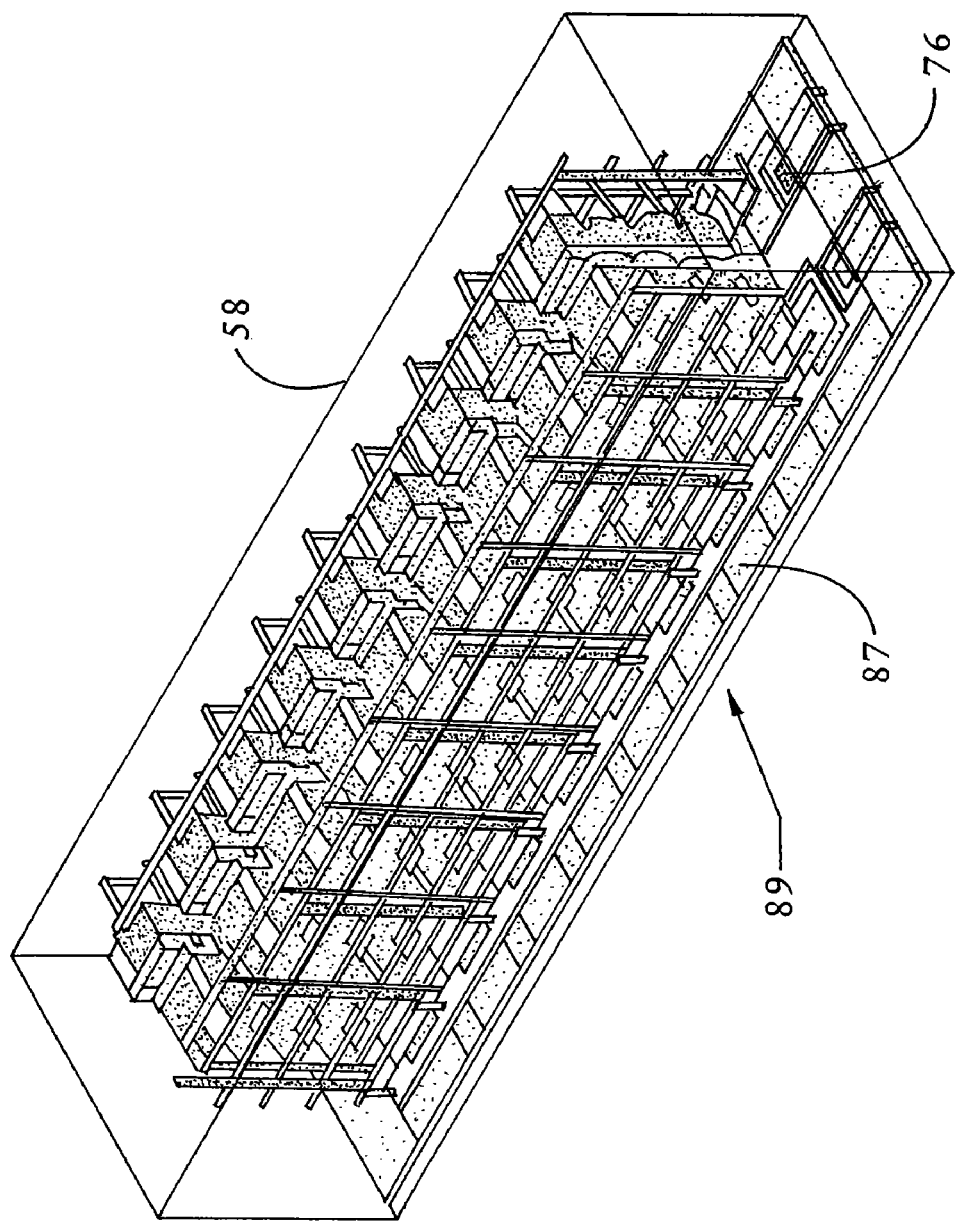
FIG. 9 illustrates a plurality of vertical sections of the single-dose dispenser.

FIG. 9 illustrates portions of a single-dose dispenser 58 in an assembled condition. Around the single-dose dispenser 58, a moving track 87 is provided for orienting the dispensing modular trays 76 to access points 89 accessible by the transporters, such as the transport robot 60, which then transport the dispensing modular trays 76 with the single-dose containers 56 to remote locations within the care facility.

Figure 10B:
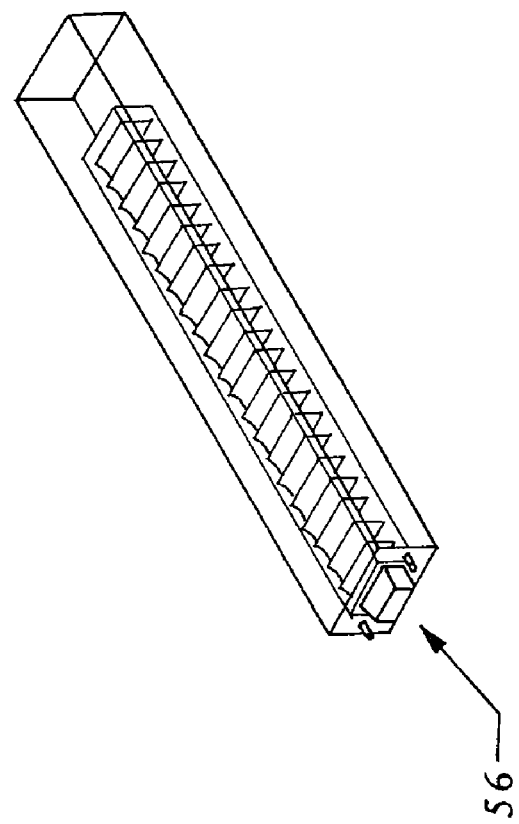
FIGS. 10A and 10B illustrate an orthogonally-shaped dose container dispenser.
Figure 10A:
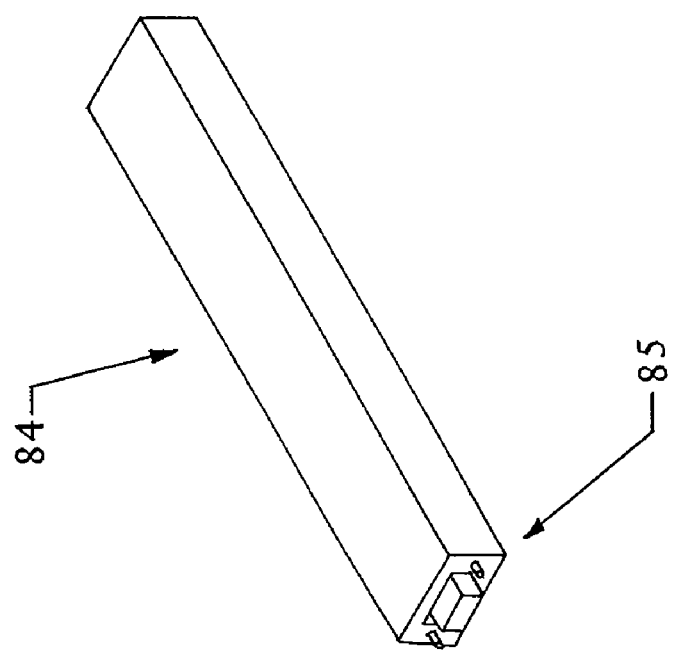

FIGS. 10A and 10B illustrate embodiments of a tray 84 for handling orthogonally-shaped single-dose containers 56. As illustrated, the tray 84 is configured to serially retain a plurality of orthogonally-shaped dose containers 56, with one of the containers 56 protruding from an end of the tray 84. FIG. 10A depicts the tray 84 with a container 56 extending from one end of the tray 84. The tray 84 is depicted as transparent in FIG. 10B to depict the serially retained containers 56 as contained in the tray 84. The end of the single-dose container 56 that protrudes from the end of the tray 84 preferably includes the above-mentioned identifier, or label 57, for providing information pertaining to the medication dose contained in the single-dose container 56. The tray 84 preferably includes one or more rods 85 extending from the tray 84 that, upon being depressed, releases the single-dose container 56 that is protruding from the tray 84.

Figure 11:
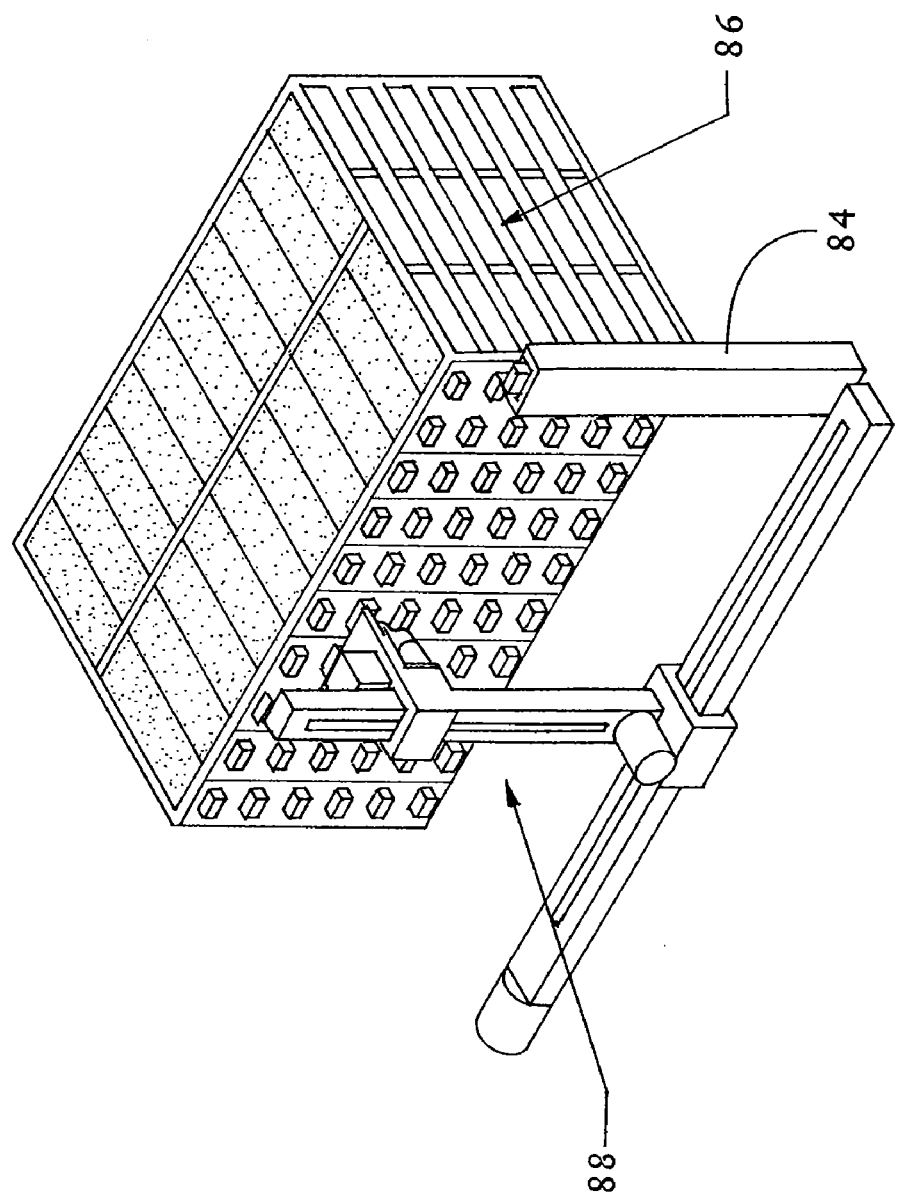
FIG. 11 illustrates embodiments of a plurality of orthogonally-shaped dose container racks and an associated picker arm and camera.

The trays 84 are preferably configured to be placed into a rack 86 that holds a plurality of trays 84, as depicted in FIG. 11. An arm 88 is preferably provided adjacent the rack 86 and is actuable to retrieve single-dose containers 56 from the trays 84. As depicted in FIG. 11, the trays 84 can be placed in a vertical orientation in order to fill the tray 84 with single-dose containers 56.

Figure 12:
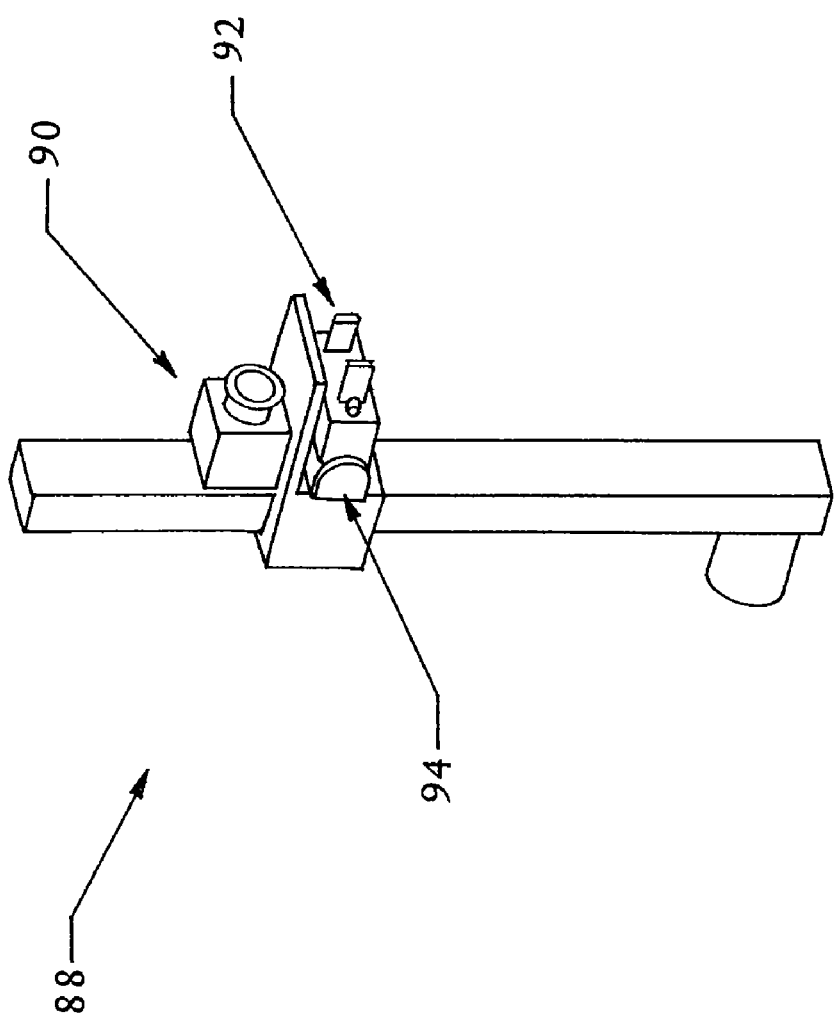
FIG. 12 illustrates embodiments of the picker arm and camera of FIG. 11.

FIG. 12 depicts a perspective view of the arm 88 that is configured to retrieve single-dose containers 56 from the trays 84. The arm 88 preferably includes a camera 90 for reading or retrieving information from the identifier, or label 57, on the containers 56. The arm 88 further includes a gripper 92 that is configured to depress the one or more rods 85 extending from the tray 84. Upon depressing the rods 85, the single-dose container 56 is released from the tray 84, and the arm 88 is able to withdraw the container 56 from within the tray 84. The gripper 92 is preferably pivotable about a pivot point 94, by which the gripper 92 is connected to the arm 88. A plurality of racks 86, and arms 88, may be combined to form a subsystem of the container dispenser 58.

Figure 13:
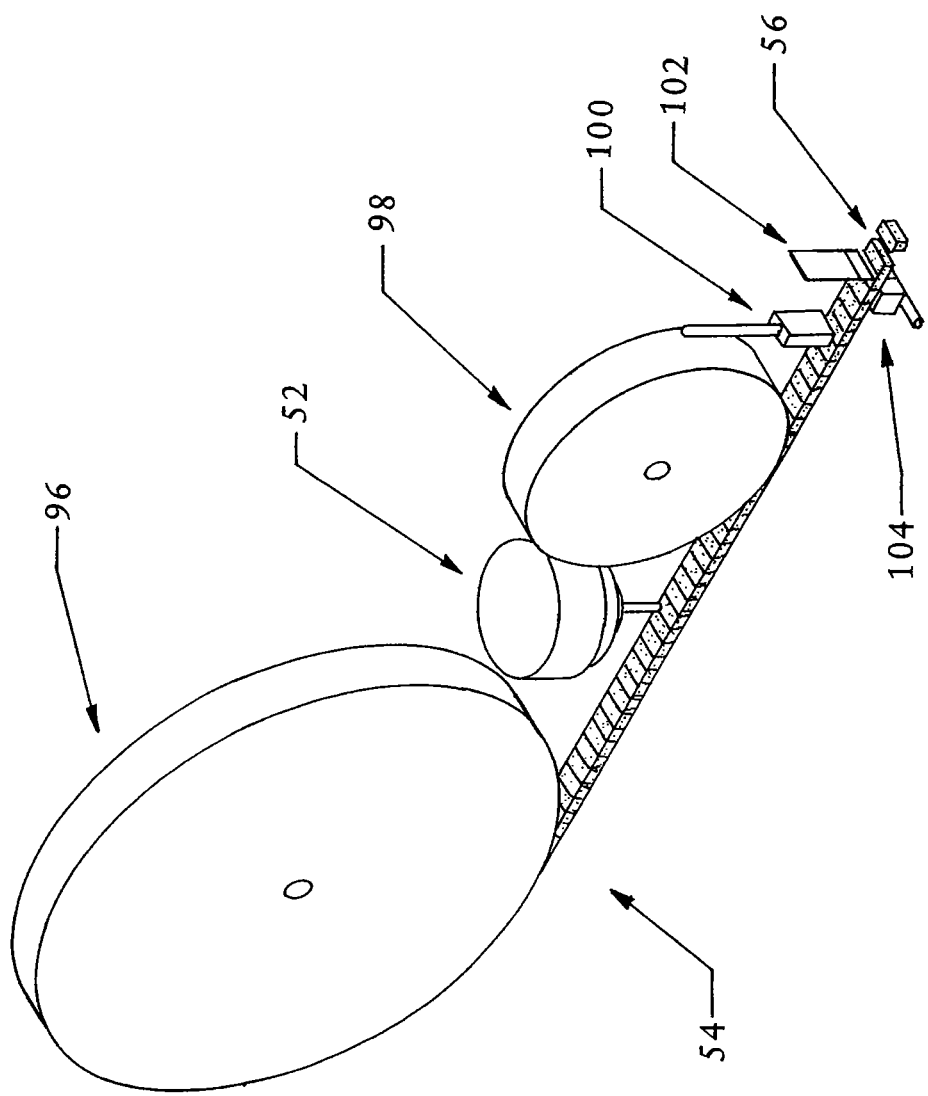
FIG. 13 illustrates a subsystem for filling and sealing orthogonally-shaped dose containers.

FIG. 13 illustrates embodiments of a drug packager 54 that packages medications in an orthogonally-shaped dose container 56. The drug packager 54 preferably includes a reel 96 of empty single-dose containers 56. The reel 96 feeds the empty single-dose containers 56 under a bulk drug container 52 that dispenses medication doses into the single-dose containers 56. The single-dose containers 56 with the medication doses disposed therein subsequently passes under a reel 98 of single-dose container covers, and the containers 56 and the covers are sealed together by a container cover heat sealer 100. The individual single-dose containers 56 are severed from the remaining reel of containers by a cutter 102. Preferably prior to being severed, the drug packager 54 includes a printer or other identifier applier 104 that provides the identifier to the single-dose container 56, thus providing an indicator of the medication provided in the container 56.

Figure 14:
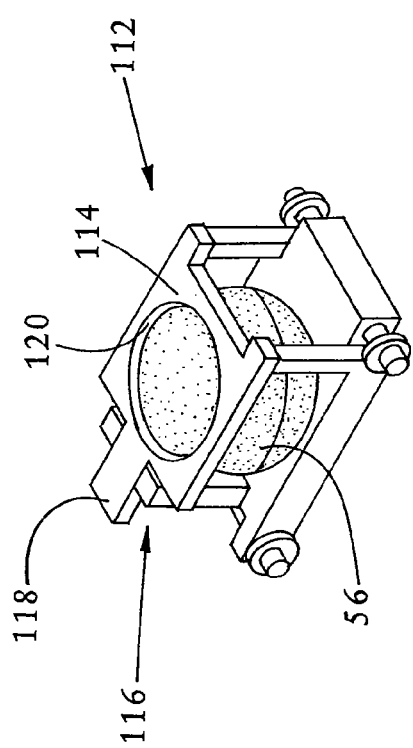
FIG. 14 illustrates embodiments of a portion for containing a single-dose container described herein.
Figure 15:
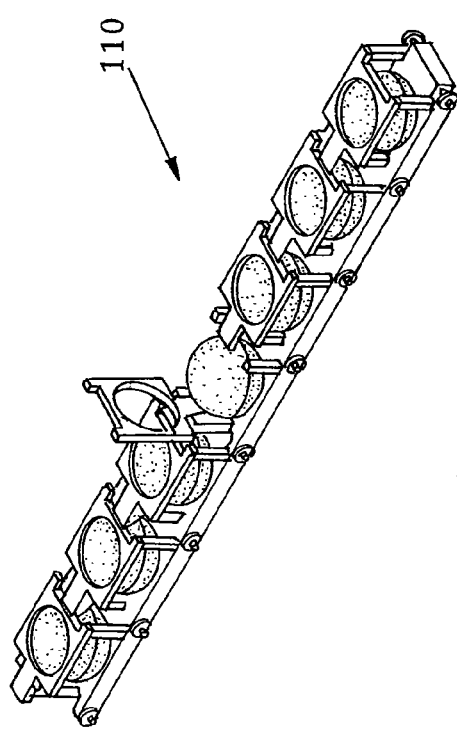
FIG. 15 illustrates embodiments of a track of a plurality of the portions depicted in FIG. 14.

FIGS. 14 and 15 depict embodiments of another system for storing and dispensing the single-dose containers 56 within the single-dose dispenser 58. FIGS. 14 and 15 illustrate a container track 110 that is configured to reside within the single-dose dispenser 58 and to handle the containers 56. In some embodiments, the container track 110 can replace the modules 65 or trays 66 for storing and relocating the containers 56. The container track 110, when located within the single-dose dispenser 58 or other storage unit, is used to store, identify, and dispense the single-dose containers 56. FIG. 14 depicts a single portion 112 of the container track 110, which is configured to handle one single-dose container 56. The single portion 112 depicted in FIG. 14 is configured to retain and handle a spherical single-dose container 56, and in other embodiments, the single portion 112 is configured to retain and handle single-dose containers 56 of different sizes and shapes. For example, the single portion 112 can be configured to retain and handle single-dose containers 56 that are orthogonally-shaped, cylindrical, pyramidal, or that are other regular or irregular shapes. Although the container track 110 is depicted as accommodating a single shape, the individual single portions 112 can be configured to interlink with single portions 112 that are configured to accommodate different shapes. Accordingly, the container track 110 can include different single portions 112 that can accommodate single-dose containers 56 having different sizes and shapes. A processor 51 (depicted in FIG. 23) preferably obtains or retains information from about the single portion 112 and apportions single-dose containers 56 with accommodating single portions 112.

In some embodiments, as depicted in FIG. 14, the single portion 112 includes a top portion 114 that retains the single-dose container 56 within the single portion 112 when the top portion 114 is in a closed position. The top portion 114 is preferably rotatable about a pivot 116, and upon rotating about the pivot 116 from the closed position, the top portion 114 opens to provide access to the single-dose container 56. The top portion 114 includes, in some embodiments, an actuator 118, such as, for example, a leverage tab, that operates to effect the opening and closing of the top portion 114. Accordingly, when the single-dose container 56 is positioned within the single portion 112, the top portion 114 is in a closed position, and when the single-dose container 56 is to be retrieved from the single portion 112, the actuator 118, such as a leverage tab, is used to open the top portion 114 and allow access to the single-dose container 56, as depicted in FIG. 15. In some embodiments, as depicted in FIG. 14, the top portion 114 includes an aperture 120, or other means, to permit visual or other detection of the label 57 or identifier of the single-dose container 56 when the top portion 114 is in a closed position.

Figure 18:
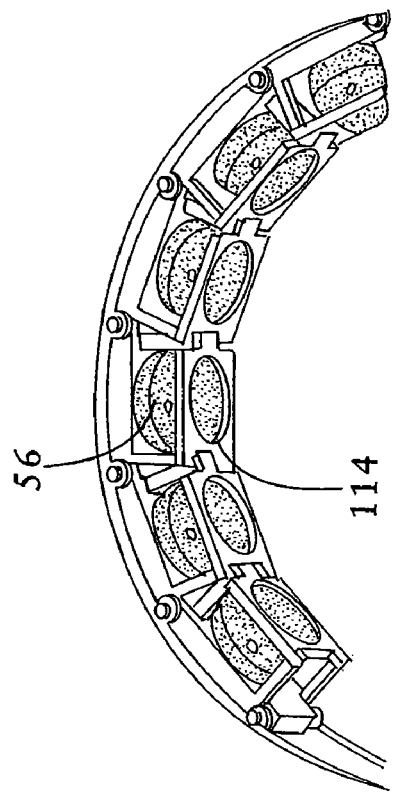
FIG. 18 illustrates embodiments of a track of a plurality of the portion depicted in FIG. 14 extending around a curve.
Figure 17:
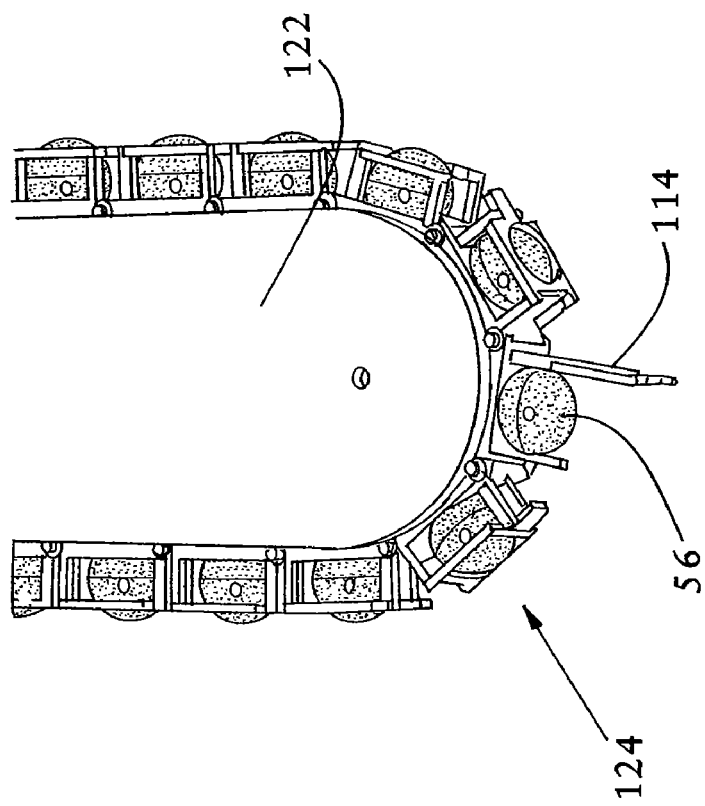
FIG. 17 illustrates embodiments of a track of a plurality of the portion depicted in FIG. 14 extending around a dispensing curve.

FIG. 16 depicts a rack 122 for operation with the container track 110. The illustrated rack 122 includes four dispensing arcs 124, where the top portions 114 of the single portions 112 can be opened and release the single-dose container 56. As can be seen with respect to FIGS. 17 and 18, when the rack 122 is positioned in a vertical orientation, with the dispensing arcs 124 facing downward, when the top portions 114 are in an opened configuration, the single-dose containers 56 will fall from the single portion 112. The top portions 114 also keep the single-dose containers 56 retained within the single portion 112 at other locations of the rack 122, such as illustrated in FIG. 18.

Figure 19:
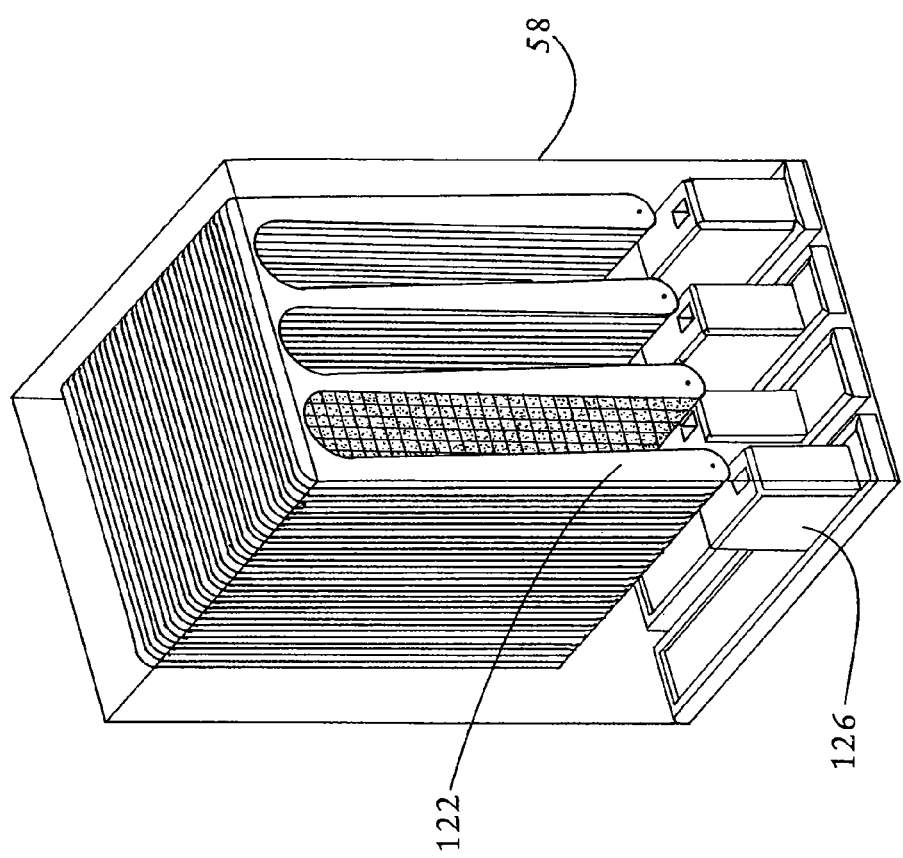
FIG. 19 depicts embodiments of a plurality of tracks that are configured to dispense single-dose containers into dispensing modules.

A plurality of racks 122 that hold container tracks 110 can be used together in the single-dose dispenser 58, as depicted in FIG. 19. The plurality of racks 122 can be configured to provide single-dose containers 56 to dispensing modules 126 positioned adjacent to the racks 122. In the embodiments illustrated in FIG. 19, the dispensing modules 126 are positioned below the racks 122 such that when the single-dose containers 56 are released from the single portion 112, the single-dose containers 56 fall into the dispensing modules 126. Once the dispensing modules 126 are filled with requested single-dose containers 56, then a transporter, such as a transport robot 60, conveys the dispensing modules 126 to the specified locations within the care facility.

Figure 20:
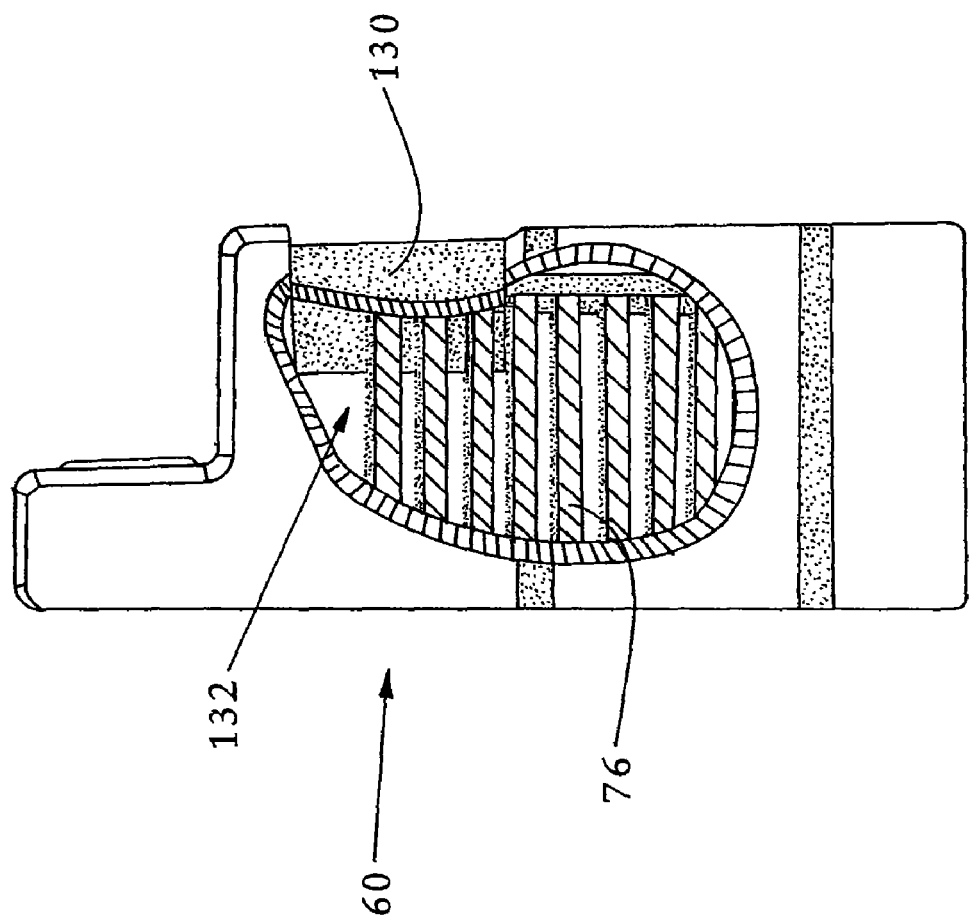
FIG. 20 illustrates a cut-away view showing embodiments of an inside portion of a transport robot.

When the single-dose containers 56 leave the single-dose dispenser 58, some embodiments provide that the containers 56 are conveyed by a transporter to a specified location within the care facility. As described above, in some embodiments, the single-dose containers 56 are handled during this conveyance to the specified locations in a dispensing modular tray 76 or a dispensing module 126. Depicted in FIG. 20 are embodiments of a transport robot 60 that is used, in some embodiments, to convey the single-dose containers 56 to and from specified locations within the care facility. As illustrated in the cut-away portion of FIG. 20, the transport robot 60 preferably includes an access port 130 that provides access into an internal portion 132 of the transport robot 60. When the transport robot 60 retrieves dispensing modular trays 76 and/or dispensing modules 126, the access port 130 is opened, and the trays 76 and/or modules 126 are received into the internal portion 132. The trays 76 and/or modules 126 are retained within the internal portion 132 until the transport robot 60 is positioned and prepared to deliver the trays 76 and/or modules 126 at the specified location to which they are to be delivered.

Although FIG. 20 illustrates a transporter that contains the single-dose containers 56 within an internal portion of the transporter, the transporter can, in some embodiments, handle the single-dose containers 56 in a location that is not internal to the transporter. For example, the transporter can convey the single-dose containers 56 on top of the transporter. It is preferred, however, that during conveyance of the single-dose containers 56 to and from the single-dose dispenser 58, the containers 56 be provided in a secure location that is resistant to tampering or unauthorized access.

When the transporter, or transport robot 60, has conveyed the dispensing modular trays 76 and/or dispensing modules 126 to the specified location within the care facility, the transport robot 60 preferably ports, or docks, with a storage device 62. The storage devices 62 are preferably positioned near caregiver stations and operate to locally retain medication doses for treatment of patients within a particular region of the care facility. For example, a caregiver station 174 (schematically depicted in FIG. 23) may be a central location for a plurality of patients, and medication doses can be provided for each of the patients within the region of the care facility by storing them in the storage device 62. Caregivers are given authority to access and administer to patients the medication doses contained within the storage device 62.

Figure 21:
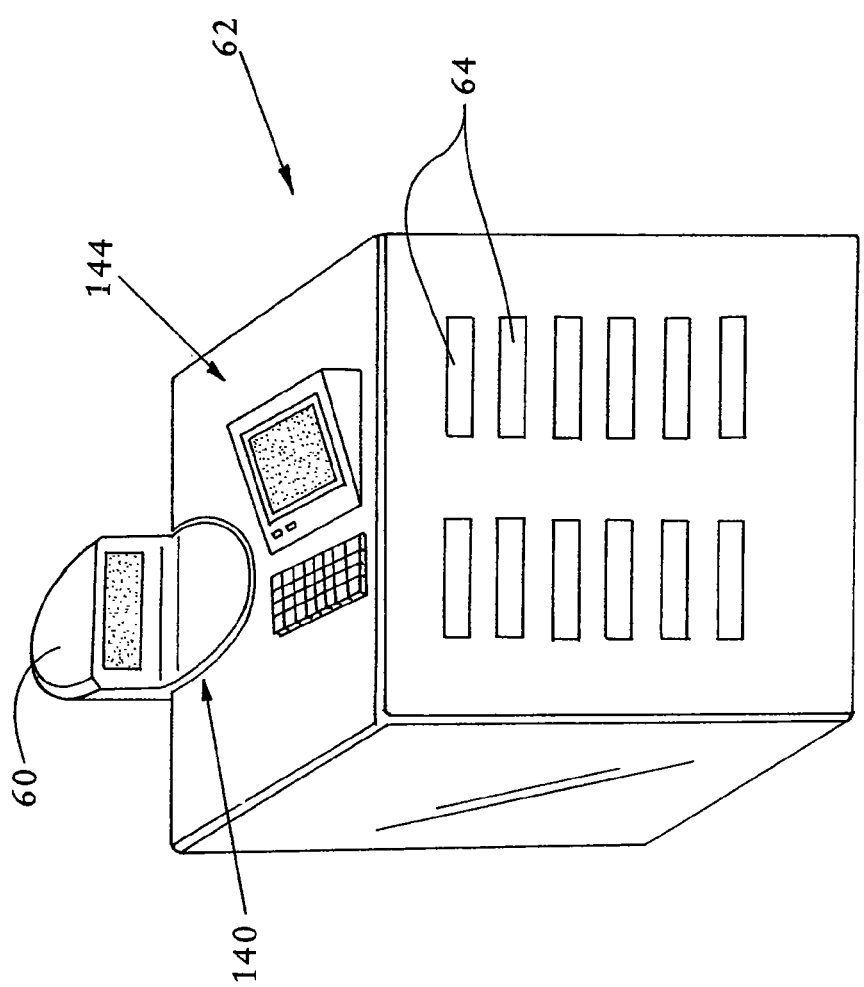
FIG. 21 illustrates embodiments of a storage device coupled to a transport robot.

With reference to FIG. 21, a storage device 62 is depicted. In some embodiments, the storage device 62 includes an access portion 140 that is configured to provide access to the storage device 62 by a transport robot 60. The transport robot 60 preferably ports with the storage device 62 at the access portion 140 and delivers the dispensing modular trays 76 and/or dispensing modules 126 through the access port 130 of the transport robot 60. The transport robot 60 is also configured to received trays 76 and/or modules 126 from the storage device 62 and, among other things, return the trays 76 and/or modules 126 to the single-dose dispenser 58 or convey the trays 76 and/or modules 126 to a different location within the care facility.

In some embodiments, the storage device 62 includes at least one dockable hand-carried dispenser 64 that can be programmed to receive single-dose containers 56 from the storage device 62. In some embodiments, each hand-carried dispenser 64 corresponds to a patient, and the hand-carried dispenser 64 retrieves from the storage device 62 those medication doses that are scheduled or desirable for that patient. In other embodiments, each hand-carried dispenser 64 corresponds to a particular caregiver and the patients to whom the caregiver is or will be administering. For example, the caregiver may access the hand-carried dispenser 64 prior to visiting the patients under his or her care. Upon preprogramming of the specific medications to be administered, the hand-carried dispenser 64 preferably obtains from the storage device 62 the medications that are scheduled, or are likely to be requested, for the patients under his or her care.

The storage device 62 can further provide an input device 144, or user interface device, that is configured to permit the caregiver to input information regarding requested medications or other patient needs. In some embodiments, the input device 144 controls a security mechanism (not shown) that limits access to the hand-carried dispensers 64. In some embodiments, as depicted in FIG. 21, the input device 144 can include, for example, a liquid crystal display (LCD) monitor and a keyboard for inputting information. In other embodiments, the input device 144 can include other device for inputting information, such as, for example, microphones, cameras, touch screens, and/or a central processing unit.

Figure 22:
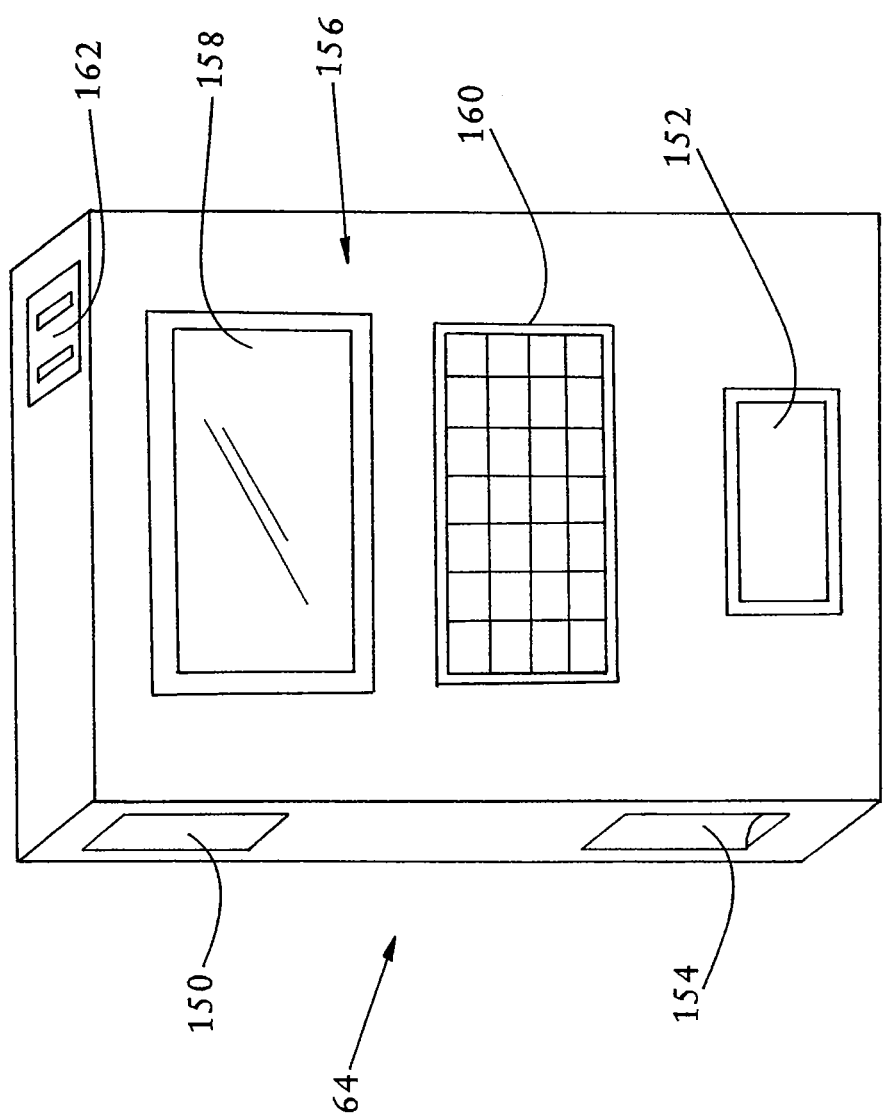
FIG. 22 illustrates embodiments of a hand-held dispenser for containing and dispensing medication doses.

FIG. 22 illustrates embodiments of the hand-carried dispenser 64. In some embodiments, the hand-carried dispenser 64 includes a receiver port 150 that is configured to receive single-dose containers 56 when the hand-carried dispenser 64 is docked with the storage device 62. The hand-carried dispenser 64 also preferably includes a medication dispenser portal 152 that provides medication doses when requested by the caregiver. In some embodiments, the hand-carried dispenser 64 is configured to remove the medication dose from the single-dose container 56. In such embodiments, the hand-carried dispenser 64 can remove the medication dose and separate the dose from the single-dose container 56. The medication dose is preferably removed by the caregiver from the medication dispenser portal 152, and the empty single-dose container 56 can be removed from a disposal portal 154. In other embodiments, the single-dose container 56 containing the medication dose can be removed from the medication dispenser portal 152, and the medication dose can subsequently be removed from the single-dose container 56.

Some embodiments of the hand-carried dispenser 64 include a user interface 156 that is capable of receiving input and instructions from a caregiver. For example, as depicted in FIG. 22, some embodiments of the hand-carried dispenser 64 include an LCD screen 158 for viewing by the caregiver and a touchpad 160 for providing instructions or other inputs into the hand-carried dispenser 64. In some instances, each patient can have a predetermined medication regimen, and the caregiver can access any particular regimen by identifying for which patient the caregiver is seeking medication. By inputting the patient's name or other identifying information through the user interface 156, the hand-carried dispenser 64 can display which medications are to be dispensed. In some embodiments, the hand-carried dispenser 64 includes a dispensing command that operates, upon indication, to automatically remove the medication dose from the single-dose container 56 and dispense the medication dose from the mediation dispenser portal 152.

The hand-carried dispenser 64 preferably includes, in some embodiments, an electrical connector 162 that is configured to provide an electrical connection between the hand-carried dispenser 64 and the storage device 62. The electrical connector 162 can be used, in some embodiments, to charge internal batteries within the hand-carried dispenser 64 so that when the caregiver removes the hand-carried dispenser 64 from the storage device 62, the hand-carried dispenser 64 has an internal power source. In further embodiments, the electrical connector 162 provides an electrical connection between the storage device 62 and the hand-carried dispenser 64 for sharing information between the two subsystems 62, 64. For example, in some embodiments, a caregiver provides instructions regarding the hand-carried dispenser 64 through the input device 144 of the storage device 62. These instructions can be transferred to the hand-carried dispenser 64 through the electrical connector 162 and utilized when the hand-carried dispenser 64 is no longer docked with the storage device 62.

While embodiments described above with respect to the hand-carried dispenser 64 provide that the hand-carried dispenser 64 be operated in connection with the storage device 62, in some embodiments, the hand-carried dispenser 64 can operate without the storage device 62. For example, in some embodiments, the hand-carried dispenser 64 can dock directly with the transport robot 60 or the single-dose dispenser 58. In some embodiments, a hand-carried dispenser 64 is provided outside of each patient's room. For example, each patient can be provided with a hand-carried dispenser 64 on a wall just outside each patient's room. In some embodiments, the hand-carried dispenser 64 is configured to dock with, and be removable from, a unit built into or onto the wall, and in some embodiments, the dispenser 64 is a fixed unit built into or onto a wall adjacent patients' rooms that provides access both to the transport robot 60, for receiving the single-dose containers 56, and to a caregiver, for retrieving the containers 56 or medication from the dispenser 64. The dispenser 64 can be configured to permit coupling with the transport robot 60, which can stop at each patient's dispenser 64 and stock the respective dispenser 64 with the patient's specific medication doses. Accordingly, as the caregiver approaches each patient's room, the caregiver can check to see whether the patient requires administration of medication, and if so, the caregiver can obtain them immediately from the dispenser 64 and administer them to the patient.

Figure 23:
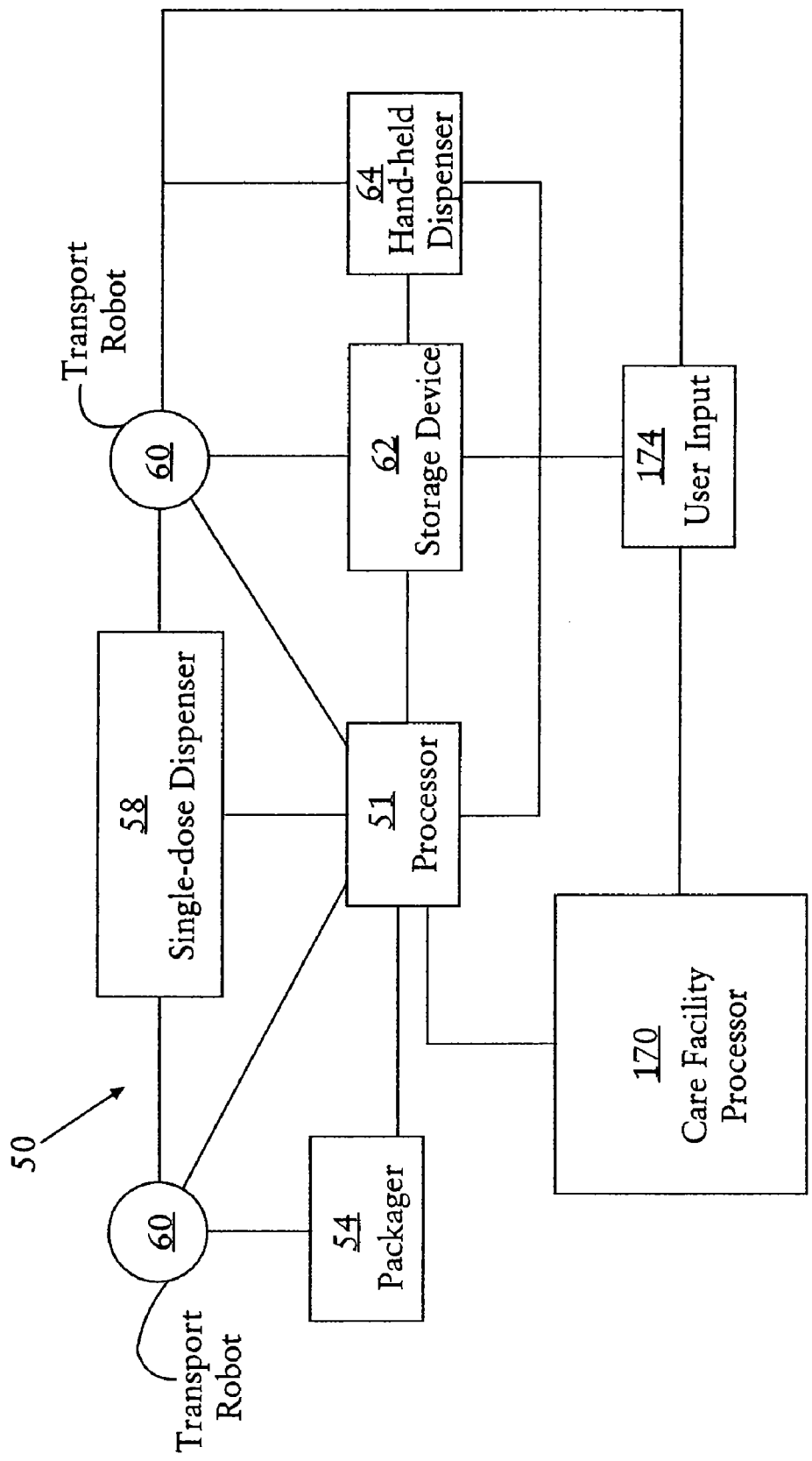
FIG. 23 provides a schematic representation of embodiments of communication channels that can be used to communicate between subsystems.

FIG. 23 depicts several embodiments for communication between the several subsystems of the automated medication handling system 50. Communication between the subsystems can be accomplished via cables, wires, and other connections with which the components interact or are coupled. For example, when the transport robot 60 docks with the single-dose dispenser 58, communication between the transport robot 60 and the single-dose dispenser 58 can be accomplished through an electrical connection that is shared between the transport robot 60 and the single-dose dispenser 58. In other embodiments, communication between the subsystems can be accomplished via wireless communication. For example, some or all of the subsystems can have transmitters for communicating information and receivers for receiving information regarding the operations of other subsystems. In yet further embodiments, a combination of hard-wired communications and wireless communications can also be employed.

In some embodiments, a processor 51 is provided to coordinate locating, storing, relocating, retrieving, and dispensing of the medication doses. In some embodiments, as depicted in FIG. 23, the processor 51 is preferably configured to communicate, either by wire or wireless communication, to some, if not all, of the subsystems. For example, the processor 51 can coordinate the transfer of medication doses from the packager 54 to the single-dose dispenser 58 via a transporter, or a transport robot 60.

The processor 51 can provide instructions relating to the positioning of the medication doses with the single-dose dispenser 58 and can communicate with a main care facility processor 170, which, in some embodiments, can contain a database for retaining information relating to the medication doses. The processor 51 can also coordinate the transfer of medication doses from the single-dose dispenser 58 to the storage devices 62 and the hand-held dispensers 64.

In some embodiments, the processor 51 is configured to communicate with a user input 174, such as a caregiver terminal, a storage device input device 144, and/or a user interface 156 of the hand-held dispenser 64. For example, a caregiver could provide a request for a certain medication dose, and the processor 51 can provide instructions to the single-dose dispenser 58 to provide the medication dose to a robot 60 to deliver to the caregiver or storage device 62.

In yet further embodiments, the processor 51 is configured to provide instructions to some subsystems, while various subsystems may also contain processors and provide instructions to other subsystems. For example, in some embodiments, the single-dose dispenser 58 can instruct the transport robots 60 to transport medication doses to or retrieve medication doses from the storage devices 62.

The processor 51 is configured to, in some embodiments, keep track of each single-dose container 56 within the system 50, and the processor 51 can retain information regarding each container 56. For example, the processor 51 can conduct an analysis on which medication doses are nearing an expiration date and reposition the medications within the care facility to use the older medication doses. Among other ways of accomplishing retrieval of older medication doses, the processor 51 can instruct the storage device 62 to provide older medication doses to the transport robot 60, which can return the older medication doses to the single-dose dispenser 58. From this point, the older medication doses can be removed from the system 50 if they have expired. If the medication doses have not expired, the older medication doses can be positioned by a transport robot 60 directly into a hand-held dispenser 64 or in a position within a storage device 62 such that the older medication will be used first. In this way, the processor 51 can manage the medication doses within the system 50 and can have access to any one medication dose upon demand. Accordingly, embodiments described above and those depicted in the figures provide an automated medication handling system 50 that can package, label, store, locate, transport, and dispense medication doses throughout a care facility.

Although preferred embodiments of the disclosure have been described in detail, certain variations and modifications will be apparent to those skilled in the art, including embodiments that do not provide all the features and benefits described herein. It will be understood by those skilled in the art that the present disclosure extends beyond the specifically disclosed embodiments to other alternative or additional embodiments and/or uses and obvious modifications and equivalents thereof. In addition, while a number of variations have been shown and described in varying detail, other modifications, which are within the scope of the present disclosure, will be readily apparent to those of skill in the art based upon this disclosure. It is also contemplated that various combinations or subcombinations of the specific features and aspects of the embodiments may be made and still fall within the scope of the present disclosure. Accordingly, it should be understood that various features and aspects of the disclosed embodiments can be combined with or substituted for one another in order to form varying modes of the present disclosure. Thus, it is intended that the scope of the present disclosure herein disclosed should not be limited by the particular disclosed embodiments described above.

What is claimed is:

1. A system for managing medications in a care facility, comprising:
    a plurality of medication containers, each of the plurality of medication containers including at least one machine-readable identifier and configured to contain a dose of a medication and configured to allow replacement of the dose of the medication with a dose of another medication; and
    a dispenser comprising:
        a plurality of storage locations, each storage location configured to store one of the plurality of medication containers, and to allow retrieval of one of the plurality of medication containers without having to remove any of the remaining plurality of medication containers from their corresponding storage locations;
        a detector configured to read the at least one machine-readable identifier of each of the plurality of medication containers while each of the plurality of the medication containers is located in its corresponding storage location; and
        a selection device configured to retrieve each of the plurality of medication containers when the corresponding medication container falls from its corresponding storage location.

2. The system of claim 1, wherein the dispenser further comprises a processor configured to (1) store information associated with the at least one machine-readable identifier for each of the plurality of medication containers, wherein the information includes at least one of a medication name, a dosage, a manufacturer, a lot date number, and an expiration date, (2) receive an input comprising an identification of a drug and a dose of the drug to be dispensed, (3) select one of the plurality of medication containers to be retrieved that corresponds to the identified drug and the dose of the drug, and (4) identify, to the selection device, the storage location containing the selected one of the plurality of medication containers.

3. The system of claim 2, wherein the selected one of the plurality of medication containers is selected by the processor because the selected one of the plurality of medication containers has the earliest expiration date of each of the plurality medication containers that corresponds to the identified drug and the dose of the drug.

4. The system of claim 2, wherein the processor is further configured to identify, to the selection device, at least one of the plurality of medication containers that contains expired medications.

5. The system of claim 2, further comprising a transport robot that is configured to convey the plurality of medication containers between the dispenser and a storage unit comprising another plurality of storage locations, each of the another plurality of storage locations configured to store one of the plurality of medication containers.

6. The system of claim 5, wherein the processor determines which of the plurality of medication containers is to be conveyed by the transport robot based on information obtained from the detector.

7. The system of claim 1, wherein the at least one machine-readable identifier comprises at least one of a barcode, a radio-frequency identification tag, and a two-dimensional matrix.

8. The system of claim 1, further comprising a medication picker system that locates a desired one of the plurality of medication containers at a first location and secures the desired one container for transportation to a second location.

9. The system of claim 1, further comprising a tray that retains a subset of the plurality of medication containers, the tray being conveyed between a storage unit and a dispensing unit by a transport robot.

10. The system of claim 1, wherein the detector comprises a camera that obtains an image of the machine-readable identifier.

11. The system of claim 1, wherein the detector is further configured to conduct an inventory of the plurality of medication containers stored in the dispenser.

12. The system of claim 1, wherein the dispenser is further configured to receive additional medication containers, identify the additional medication containers, and store the additional medication containers without input of additional information or action by an operator.

13. The system of claim 12, wherein the dispenser positions each of the additional medication containers within the dispenser based upon information from the corresponding machine-readable identifier of the additional medication containers read by the detector.

14. A method for managing medications in a care facility, comprising:
   providing a plurality of medication containers, each of the plurality of medication containers including at least one machine-readable identifier, and configured to contain a dose of a medication, and configured to allow replacement of the dose of the medication with a dose of another medication;
   storing, in one of a plurality of storage locations within a dispenser, one of the plurality of medication containers;
   reading the at least one machine-readable identifier of one of the plurality of medication containers while the one of the plurality of medication containers is located in its corresponding storage location; and
   retrieving one of the plurality of medication containers when the corresponding medication container falls from its corresponding storage location without having to remove any of the remaining plurality of medication containers from their corresponding storage locations.

15. The method of claim 14, wherein retrieving the one of the plurality of medication containers is in response to a recall of the medication contained in the one of the plurality of medication containers.

16. The method of claim 14, further comprising relocating the retrieved one of the plurality of medication containers because the medication included in the one of the plurality of medication containers was not administered to a patient by a caregiver.

17. The method of claim 14, further comprising
   storing information associated with the at least one machine-readable identifier for each of the plurality of medication containers, wherein the information includes at least one of a medication name, a dosage, a manufacturer, a lot date number, and an expiration date,
   receiving an input comprising an identification of a drug and a dose of the drug to be dispensed; and
   selecting one of the plurality of medication containers to be retrieved, wherein the selected one of the plurality of medication containers corresponds to the identified drug and the dose of the drug,
   wherein the retrieving the selected one of the plurality of medication containers comprises identifying the storage location containing the selected one of the plurality of medication containers.

18. The method of claim 17, wherein the selected one of the plurality of medication containers is selected because the selected one of the plurality of medication containers has the earliest expiration date of each of the plurality medication containers that corresponds to the identified drug and the dose of the drug.

19. The method of claim 17, further comprising returning unused medications to the storage facility based on the expiration date associated with the medications.

20. The method of claim 14, further comprising conducting an inventory of the plurality of medication containers.

21. The method of claim 14, further comprising:
   receiving additional medication containers;
   identifying the additional medication containers; and
   storing the additional medication containers without input of additional information or action by an operator.

22. The method of claim 14, further comprising relocating the retrieved one of the plurality of medication containers to a tray within a storage facility.

23. The method of claim 22, further comprising transporting the tray based on information from the machine-readable identifier included with the one of the plurality of medication containers.

24. The method of claim 23, wherein transporting the tray comprises transporting the tray with a transport robot.

* * * * *